US011013595B2

(12) United States Patent
Levi et al.

(10) Patent No.: US 11,013,595 B2
(45) Date of Patent: May 25, 2021

(54) SEALING ELEMENT FOR PROSTHETIC HEART VALVE

(71) Applicant: Edwards Lifesciences Corporation, Irvine, CA (US)

(72) Inventors: Tamir S. Levi, Zikhron Yaakov (IL); Giolnara Pinhas, Hadera (IL); Liraz Marom, Olesh (IL); Elena Sherman, Pardes Hanna (IL); Noam Mizrahi, Irvine, CA (US); Delfin Rafael Ruiz, Irvine, CA (US); Sandip Vasant Pawar, Irvine, CA (US); Liron Tayeb, Peduel (IL)

(73) Assignee: Edwards Lifesciences Corporation, Irvine, CA (US)

( * ) Notice: Subject to any disclaimer, the term of this patent is extended or adjusted under 35 U.S.C. 154(b) by 53 days.

(21) Appl. No.: 16/100,601

(22) Filed: Aug. 10, 2018

(65) Prior Publication Data

US 2019/0046314 A1 Feb. 14, 2019

Related U.S. Application Data

(60) Provisional application No. 62/544,704, filed on Aug. 11, 2017.

(51) Int. Cl.
 *A61F 2/24* (2006.01)
 *A61F 2/00* (2006.01)

(52) U.S. Cl.
 CPC .......... *A61F 2/2415* (2013.01); *A61F 2/0077* (2013.01); *A61F 2/2409* (2013.01);
 (Continued)

(58) Field of Classification Search
 CPC .................................. A61F 2/24; A61F 2/2415
 See application file for complete search history.

(56) References Cited

U.S. PATENT DOCUMENTS 3,409,013 A 11/1968 Berry
3,548,417 A 12/1970 Kisher
(Continued)

FOREIGN PATENT DOCUMENTS

DE 2246526 A1 3/1973
DE 0144167 C 6/1985
(Continued)

OTHER PUBLICATIONS

International Search Report for International Patent Application No. PCT/US2018/046261, completed Mar. 18, 2019.
(Continued)

*Primary Examiner* — Matthew W Schall
(74) *Attorney, Agent, or Firm* — Edwards Lifesciences; Hans P. Smith

(57) ABSTRACT

An implantable prosthetic valve that is radially collapsible to a collapsed configuration and radially expandable to an expanded configuration includes an annular frame having an inflow end, an outflow end, and a longitudinal axis. A leaflet structure is positioned within the frame and secured thereto, and a sealing element is secured to the frame. The sealing element includes a first woven portion extending circumferentially around the frame. The first woven portion includes a plurality of interwoven filaments. The sealing element further includes a second woven portion extending circumferentially around the frame and spaced apart from the first woven portion along the longitudinal axis of the frame. At least a portion of the filaments exit the weave of the first woven portion and form loops extending radially outwardly from the frame.

20 Claims, 22 Drawing Sheets

(52) U.S. Cl.
CPC .... *A61F 2/2418* (2013.01); *A61F 2210/0076* (2013.01); *A61F 2230/0069* (2013.01); *A61F 2250/0069* (2013.01)

(56) References Cited

U.S. PATENT DOCUMENTS

| | | | |
|---|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |

(56) References Cited

U.S. PATENT DOCUMENTS

| Patent/Publication No. | Date | Inventor(s) |
|---|---|---|
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0190862 A1* | 7/2013 | Pintor .................. A61F 2/2433 623/2.18 |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2017/0014229 A1 | 1/2017 | Nguyen-Thien-Nhon et al. |
| 2017/0172736 A1 | 6/2017 | Chadha et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |

(56) References Cited

FOREIGN PATENT DOCUMENTS

| | | |
|---|---|---|
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A2 | 7/1998 |
| WO | 9930646 A1 | 6/1999 |
| WO | 9933414 A1 | 7/1999 |
| WO | 0018333 A1 | 4/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0214789 A2 | 5/2002 |
| WO | 0236048 A1 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009116041 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2013190862 A1 | 12/2013 |
| WO | 2015085218 A1 | 6/2015 |
| WO | 2018222799 A1 | 12/2018 |

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
H.R. Andersen "History of Percutaneous Aortic Valve Prosthesis," Herz No. 34. pp. 343-346. 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.

\* cited by examiner

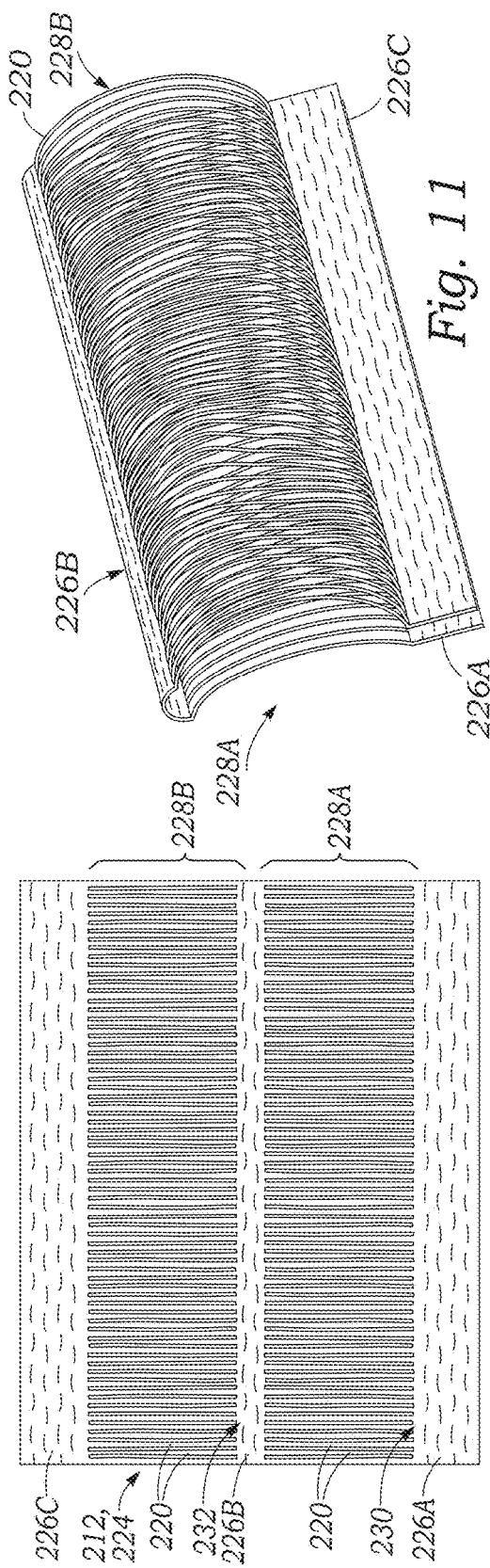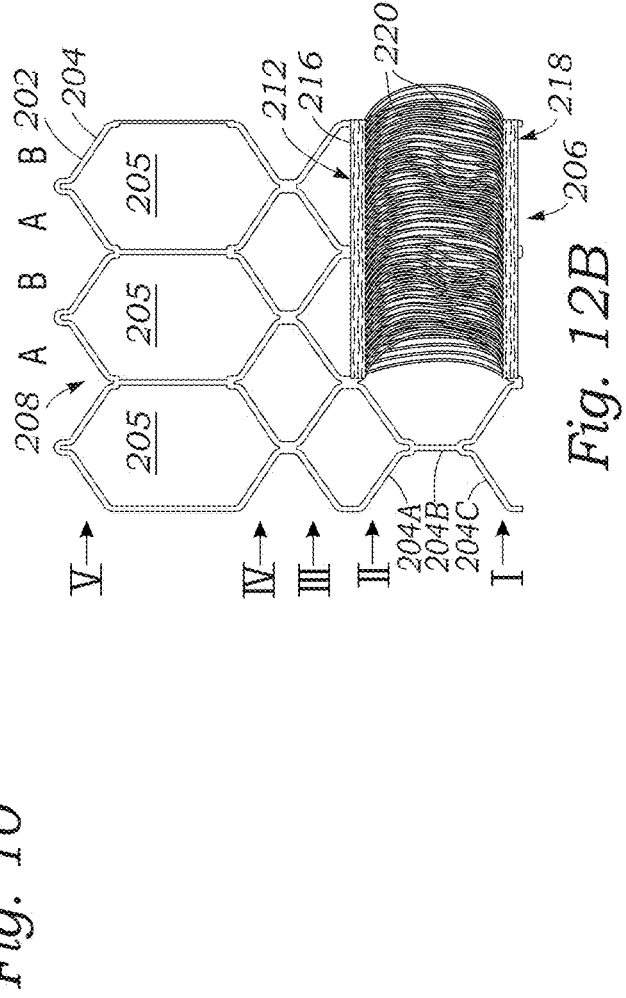

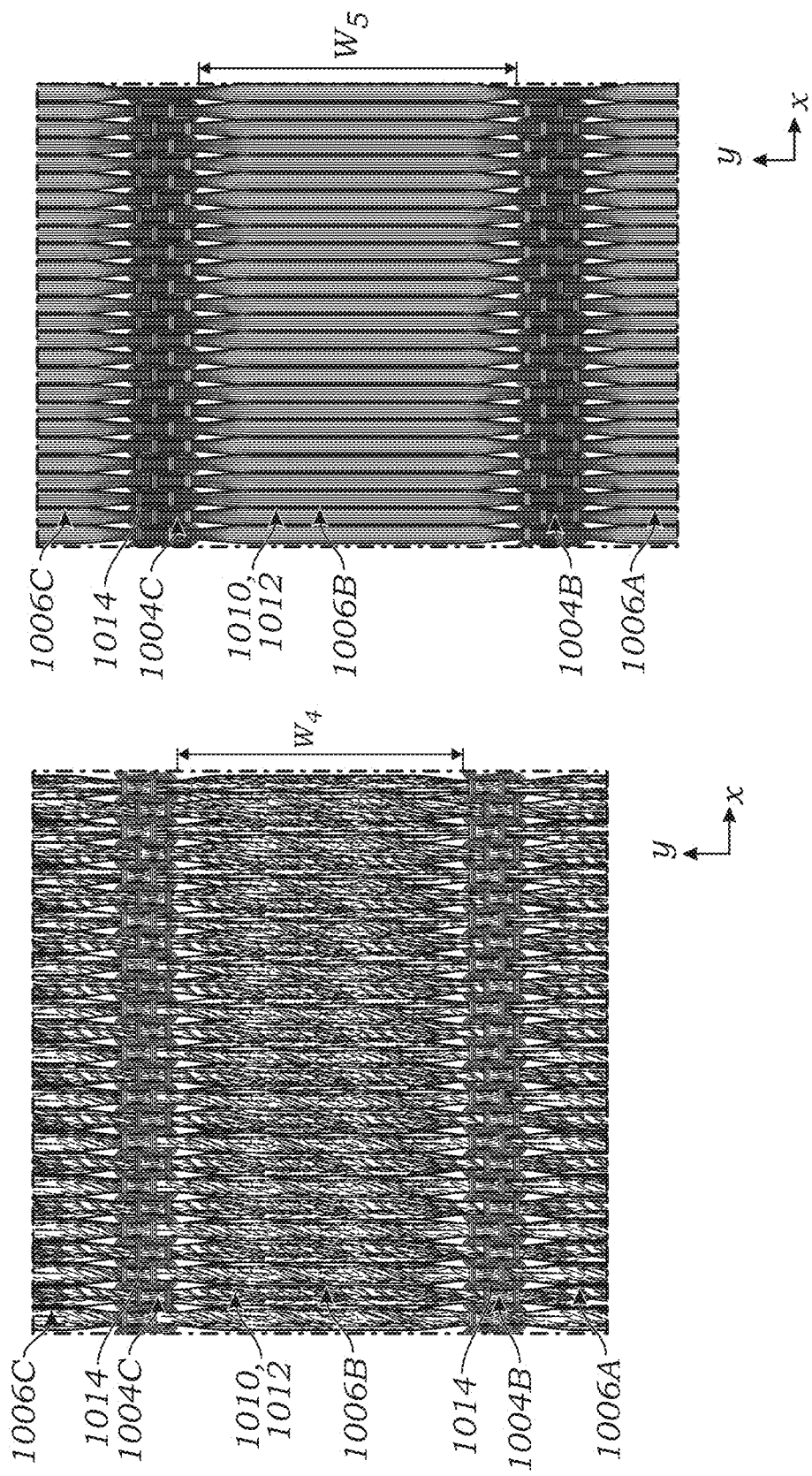

SEALING ELEMENT FOR PROSTHETIC HEART VALVE

CROSS REFERENCE TO RELATED APPLICATION

The present application claims priority to and the benefit of U.S. Provisional Application No. 62/544,704, filed on Aug. 11, 2017, which is incorporated herein by reference.

FIELD

The present application relates to embodiments of sealing elements for prosthetic heart valves and methods of making the same.

BACKGROUND

The heart can suffer from various valvular diseases or malformations that result in significant malfunctioning of the heart, and ultimately require replacement of the native heart valve with an artificial valve. Procedures in which radially collapsible transcatheter heart valves are percutaneously introduced in a compressed state on a catheter and expanded at the treatment location are gaining popularity, especially among patient populations for whom traditional surgical procedures pose a high risk of morbidity or mortality.

It can be important to reduce or prevent blood leakage past the prosthetic valve after implantation. Thus, transcatheter heart valves often include a sealing element such as a paravalvular leakage skirt to reduce the amount of leakage past the prosthetic valve. However, differences between the diameter of the prosthetic valve and the native annulus into which the valve is implanted, along with features of a particular patient's anatomy such as calcification, tissue prominences, recesses, folds, and the like, can make it difficult to achieve a seal between the prosthetic valve and the native annulus. Accordingly, there is a need for improved paravalvular sealing elements for prosthetic heart valves.

SUMMARY

Certain embodiments of the disclosure concern prosthetic valves including various embodiments of sealing elements. In a representative embodiment, an implantable prosthetic valve that is radially collapsible to a collapsed configuration and radially expandable to an expanded configuration comprises an annular frame having an inflow end, an outflow end, and a longitudinal axis. A leaflet structure is positioned within the frame and secured thereto, and a sealing element is secured to the frame. The sealing element comprises a first woven portion extending circumferentially around the frame. The first woven portion comprises a plurality of interwoven filaments. The sealing element further comprises a second woven portion extending circumferentially around the frame and spaced apart from the first woven portion along the longitudinal axis of the frame. At least a portion of the filaments exit the weave of the first woven portion and form loops extending radially outwardly from the frame.

In some embodiments, the filaments that form the loops extend from and return to the first woven portion.

In some embodiments, the first woven portion comprises a first row of loops, and the second woven portion comprises a second row of loops. The loops of the second row of loops can comprise filaments that extend from and return to the second woven portion.

In some embodiment, the loops of the second row of loops are circumferentially offset from the loops of the first row of loops.

In some embodiments, the plurality of interwoven filaments of the first woven portion further comprises at least one first filament interwoven with a plurality of second filaments, and a portion of the at least one first filament forms the loops of the first woven portion.

In some embodiments, the sealing element further comprises an intermediate sealing portion between the first and second woven portions. The intermediate sealing portion comprises a plurality of second filaments, and a portion of the at least one first filament extends along the longitudinal axis of the frame between the first woven portion and the second woven portion, and is interwoven with the second filaments of the intermediate sealing portion.

In some embodiments, a portion of the at least one first filament forms the loops of the second woven portion.

In some embodiments, the second filaments are warp yarns and the at least one first filament is a weft yarn.

In some embodiments, at least one of the warp and weft yarns comprise textured yarns.

In some embodiments, the warp and weft yarns comprise fibers having a diameter of from 1 µm to 20 µm to promote thrombus formation around the sealing element.

In some embodiments, the filaments that form the loops originate from the first woven portion and extend curvilinearly along the longitudinal axis of the frame to the second woven portion.

In some embodiments, the filaments that form the loops exit a weave of the first woven portion and are incorporated into a weave of the second woven portion such that the loops form a floating yarn portion between the first and second woven portions.

In some embodiments, the floating yarn portion comprises a first layer of loops and a second layer of loops radially outward of the first layer of loops.

In some embodiments, the sealing element comprises a first fabric strip, a second fabric strip, and a third fabric strip. A plurality of the filaments that form the loops extend between the first fabric strip and the second fabric strip, and a plurality of the filaments that form the loops extend between the second fabric strip and the third fabric strip. The sealing element is folded about the second fabric strip such that the first fabric strip and the third fabric strip are adjacent each other to form the first woven portion, the filaments extending between the first fabric strip and the second fabric strip form the first layer of loops, and the filaments extending between the second fabric strip and the third fabric strip form the second layer of loops.

In some embodiments, the sealing element is secured to the frame such that the filaments that exit the weave of the first woven portion form the loops when the frame is in the expanded configuration, and are pulled straight when the frame is in the collapsed configuration.

In another representative embodiment, a method comprises mounting any of the prosthetic valves herein to a distal end portion of a delivery apparatus, advancing the delivery apparatus through a patient's vasculature to the heart, and expanding the prosthetic valve in a native heart valve of the heart such that the prosthetic valve regulates blood flow through the native heart valve.

In another representative embodiment, a method of making a sealing element for a prosthetic heart valve comprises weaving at least one weft yarn together with a plurality of warp yarns to form a first woven portion, dropping the at least one weft yarn from a weave of the first woven portion, and looping the at least one weft yarn around a removable warp yarn. The removable warp yarn is spaced apart from the first woven portion, and the at least one weft yarn is looped around the removable warp yarn such that the at least one weft yarn extends over, and is not interwoven with, warp yarns disposed between the first woven portion and the removable warp yarn. The method further comprises reincorporating the at least one weft yarn into the weave of the first woven portion such that the at least one weft yarn forms a loop that extends from and returns to the first woven portion, and removing the removable warp yarn from the sealing element to release the loop formed by the at least one weft yarn.

In some embodiments, before removing the removable warp yarn, the method further comprises repeating the weaving, the dropping, the looping, and the reincorporating to form a plurality of loops about a circumference of the sealing element.

In some embodiments, the method further comprises shape-setting the plurality of loops such that the loops extend outwardly from the sealing element.

In some embodiments, the method further comprises before removing the removable warp yarn, weaving the at least one weft yarn together with warp yarns such that the at least one weft yarn extends beyond the removable warp yarn and forms a second woven portion spaced apart from the first woven portion. The method further comprises dropping the at least one weft yarn from a weave of the second woven portion, and looping the at least one weft yarn around a second removable warp yarn that is spaced apart from the second woven portion. The at least one weft yarn can be looped around the second removable warp yarn such that the at least one weft yarn extends over, and is not interwoven with, warp yarns disposed between the second woven portion and the second removable warp yarn. The method can further comprise reincorporating the at least one weft yarn into the weave of the second woven portion such that the at least one weft yarn forms a second loop that extends from and returns to the second woven portion.

The foregoing and other objects, features, and advantages of the disclosed technology will become more apparent from the following detailed description, which proceeds with reference to the accompanying figures.

BRIEF DESCRIPTION OF THE DRAWINGS

FIG. 10 is a top plan view of a representative embodiment of the paravalvular leakage seal of FIG. 9.

FIG. 11 is a perspective view of the paravalvular leakage seal of FIG. 9 folded over on itself prior to attachment to the prosthetic valve.

FIG. 12A is a side elevation view of a portion of the frame of the prosthetic valve of FIG. 9 in an expanded configuration illustrating the longitudinally-extending yarns of the paravalvular leakage seal curving outwardly from the frame.

FIG. 12B is a side elevation view of the portion of the frame of FIG. 12A in a radially collapsed configuration illustrating the longitudinally-extending yarns of the paravalvular leakage seal pulled straight along a longitudinal axis of the valve.

FIG. 35 is a magnified view of a floating yarn portion of the sealing member of FIG. 32 in a relaxed state.

FIG. 36 illustrates the floating yarn portion of FIG. 35 in a stretched state.

DETAILED DESCRIPTION

The present disclosure concerns embodiments of sealing elements for implantable prosthetic devices, such as prosthetic heart valves. The present inventors surprisingly have discovered that effective sealing can be accomplished by sealing elements including a plurality of filaments, such as yarns and/or fibers, that extend from the sealing element and are configured to prompt a biological response at the cellular level to promote thrombogenesis around the sealing element.

For example, the sealing elements described herein can be configured as fabric skirts including woven portions from which filaments or yarns extend, and which can contact and/or conform to the surrounding anatomy to enhance the sealing properties of the skirt. In certain configurations, the filaments are bound at both ends and form loops that extend radially outwardly from the skirt. As used herein, the term "loop" refers to a closed or partially open curve formed by a yarn or other filament. In some embodiments, the yarns that form the loops extend from and return to the same fabric portion of the skirt. In such configurations, the loops can be arranged in one or more rows extending circumferentially around the skirt. In other configurations, the yarns extend from one fabric portion to another spaced-apart fabric portion such that the loops are arrayed circumferentially around the valve and are oriented along a longitudinal axis of the valve. In still other embodiments, the filaments are bound at one end, and have free ends that extend outwardly from the skirt.

In such configurations, the filaments can be configured to slow retrograde blood flow past the valve. Features such as the diameter, shape, surface texturing, coatings, etc., of the filaments can induce thrombus formation around the filaments to enhance the sealing properties of the skirt.

Figure 1:
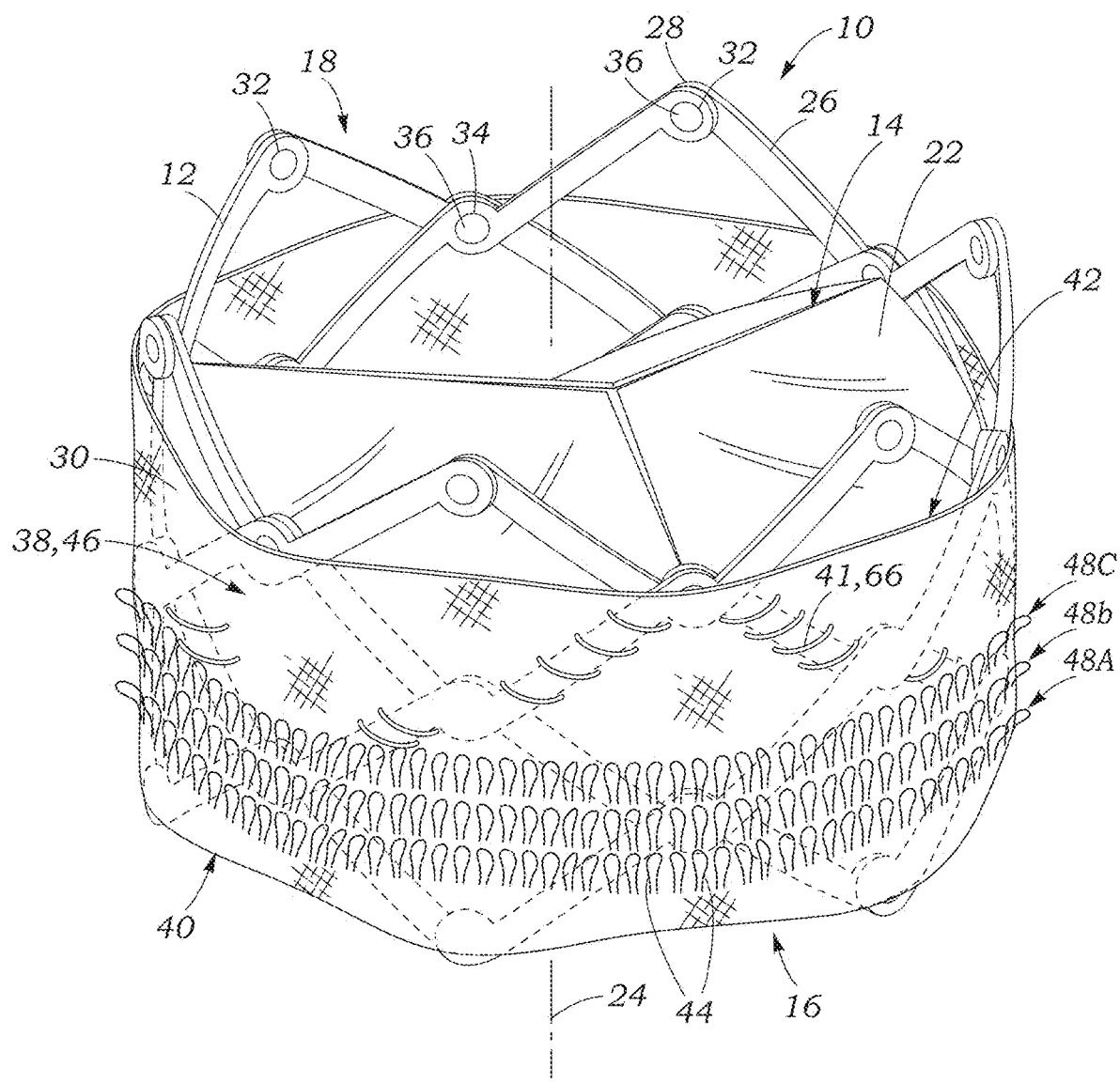
FIG. 1 is a perspective view of a prosthetic heart valve including a representative embodiment of a paravalvular leakage seal including looped filaments.

FIG. 1 illustrates an exemplary embodiment of a radially collapsible and expandable prosthetic valve 10 shown in its deployed, expanded configuration. The prosthetic valve can include an annular stent or frame 12, and a leaflet structure 14 situated within and coupled to the frame 12. The frame 12 can have an inflow end portion 16 and an outflow end portion 18. The leaflet structure can comprise a plurality of leaflets 22, such as three leaflets arranged to collapse in a tricuspid arrangement similar to the aortic valve. Alternatively, the prosthetic valve can include two leaflets 22 configured to collapse in a bicuspid arrangement similar to the mitral valve, or more than three leaflets, depending upon the particular application. The prosthetic valve 10 can define a longitudinal axis 24 extending through the inflow end portion 16 and the outflow end portion 18.

The frame 12 can be made of any of various biocompatible materials, such as stainless steel or a nickel titanium alloy ("NiTi"), for example Nitinol. With reference to FIG. 1, the frame 12 can include a plurality of interconnected lattice struts 26 arranged in a lattice-type pattern and forming a plurality of apices 28 at the outflow end 18 of the prosthetic valve. The struts 26 can also form similar apices at the inflow end 16 of the prosthetic valve (which are covered by a skirt 30 described in greater detail below). The lattice struts 26 are shown positioned diagonally, or offset at an angle relative to, and radially offset from, the longitudinal axis 24 of the prosthetic valve. In other implementations, the lattice struts 26 can be offset by a different amount than depicted in FIG. 1, or some or all of the lattice struts 26 can be positioned parallel to the longitudinal axis of the prosthetic valve.

The lattice struts 26 can be pivotably coupled to one another. In the illustrated embodiment, for example, the end portions of the struts 26 forming the apices 28 at the outflow end 18 and at the inflow end 16 of the frame can have a respective opening 32. The struts 26 also can be formed with apertures 34 located between the opposite ends of the struts. Respective hinges can be formed at the apices 28 and at the locations where struts 26 overlap each other between the ends of the frame via fasteners 36, which can comprise rivets or pins that extend through the apertures 32, 34. The hinges can allow the struts 26 to pivot relative to one another as the frame 12 is expanded or contracted, such as during assembly, preparation, or implantation of the prosthetic valve 10. For example, the frame 12 (and, thus, the prosthetic valve 10) can be manipulated into a radially compressed or contracted configuration, coupled to a delivery apparatus, and inserted into a patient for implantation. Once inside the body, the prosthetic valve 10 can be manipulated into an expanded state and then released from the delivery apparatus, as described in greater detail below with reference to FIG. 21. Additional details regarding the frame 12, the delivery apparatus, and devices and techniques for radially expanding and collapsing the frame can be found in U.S. Publication No. 2018/0153689, which is incorporated herein by reference.

As illustrated in FIG. 1, the prosthetic valve 10 can include a sealing element configured as a skirt 30. The skirt 30 can be configured to establish a seal with the native tissue at the treatment site to reduce or prevent paravalvular leakage. The skirt 30 can include a main body portion 38 disposed about an outer circumference of the frame 12. The skirt 30 can be secured to the frame by, for example, a plurality of sutures 41 extending in a zig-zag pattern along selected strut members 26 between a first edge portion (e.g., an inflow edge portion) 40 and a second edge portion (e.g., an outflow edge portion) 42 of the skirt 30. For example, in certain embodiments the skirt 30 can be sutured to the frame 12 along a suture line 66 corresponding to a scalloped edge defined by the leaflets 22, which can allow the valve to radially expand and contract without interference from, or pinching of, the skirt. Further details regarding transcatheter prosthetic heart valves, including the manner in which the leaflets 22 can be coupled to the frame 12 can be found, for example, in U.S. Pat. Nos. 6,730,118, 7,393,360, 7,510,575, 7,993,394, and 8,652,202, which are incorporated herein by reference in their entireties.

In the illustrated embodiment, the skirt 30 can comprise a plurality of outwardly extending filaments configured as loops 44 (also referred to as looped filaments). The loops 44 can extend from an outer surface 46 of the main portion 38. In certain embodiments, the loops 44 can be arranged in rows or tiers 48 that extend circumferentially around the frame 12, and are spaced apart from one another along the longitudinal axis 24. For example, in the illustrated embodiment, the loops 44 are arranged in three rows 48, with a first row 48A being adjacent the inflow edge portion 40 of the skirt, and the rows 48B, 48C being located above the first row 48A along the longitudinal axis 24 of the valve. In other embodiments, the skirt 30 can include more or fewer rows of loops, depending upon the particular characteristics desired. For example, the skirt 30 can include a single row of loops 44 (e.g., adjacent the inflow end of the frame), or a plurality of rows of loops along substantially the entire height dimension of the skirt 30.

Figure 2:
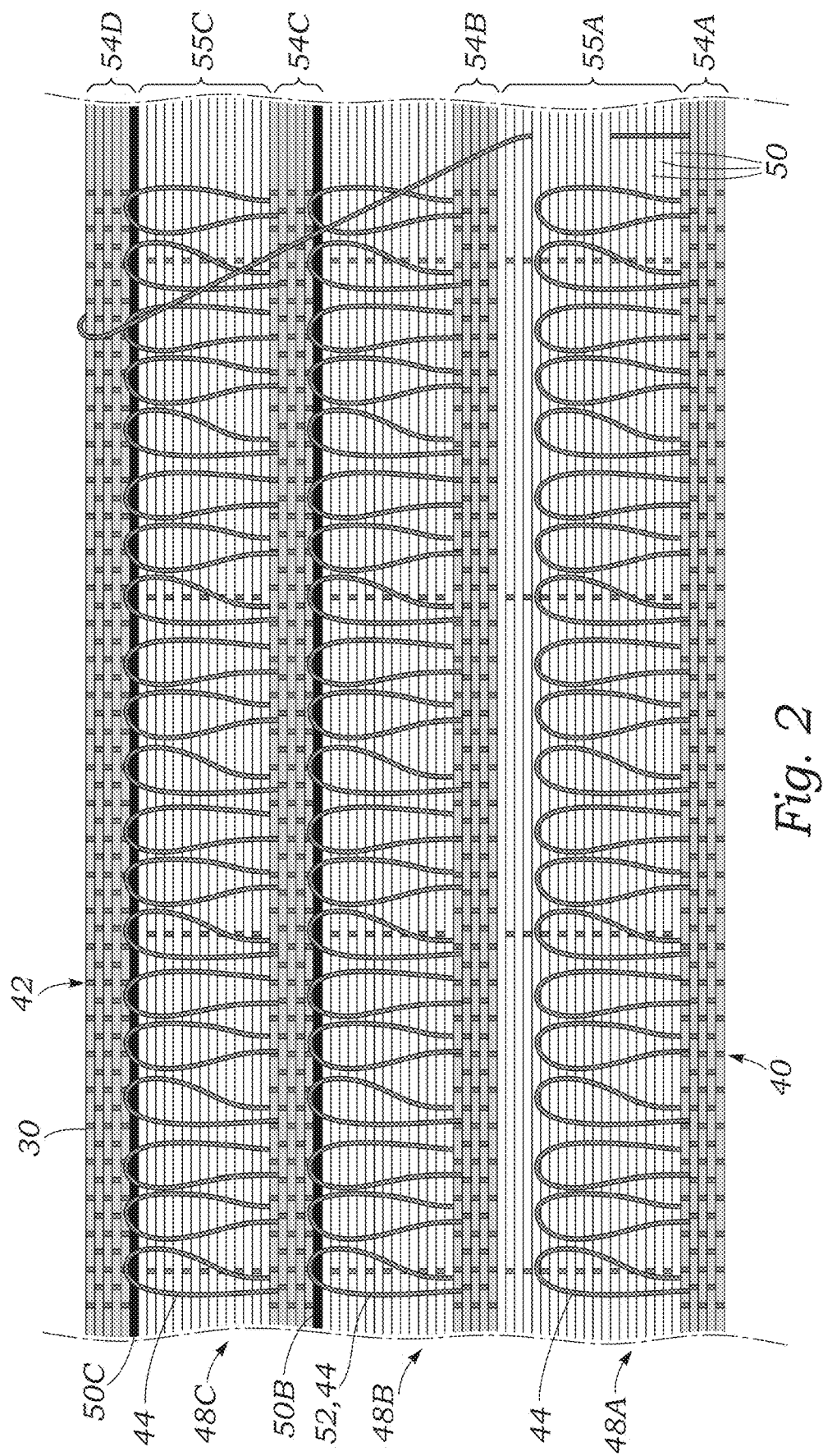
FIG. 2 is a perspective view of the paravalvular leakage seal of FIG. 1.

In particular embodiments, the skirt 30 can comprise a cloth material, such as a woven or knitted fabric. FIG. 2 illustrates a portion of a representative embodiment of the skirt 30 made from such a fabric in greater detail. The fabric can comprise a plurality of first yarns 50 oriented horizontally in FIG. 2 and one or more second yarns 52 oriented vertically in FIG. 2 and selectively interwoven with the first yarns 50 on a loom. In certain configurations, the first yarns 50 can be warp yarns, meaning that during the weaving process the yarns 50 are held by the loom, while the second yarns 52 are weft yarns, which are interwoven with the warp yarns by a moving shuttle or weft-carrying mechanism during the weaving process. However, in other embodiments the first yarns 50 may be weft yarns and the second yarns 52 may be warp yarns. In the illustrated configuration, the fabric comprises a single weft yarn 52 that is selectively interwoven with the warp yarns 50 to form the looped filaments 44, although in other embodiments more than one weft yarn may be used.

Figure 3:
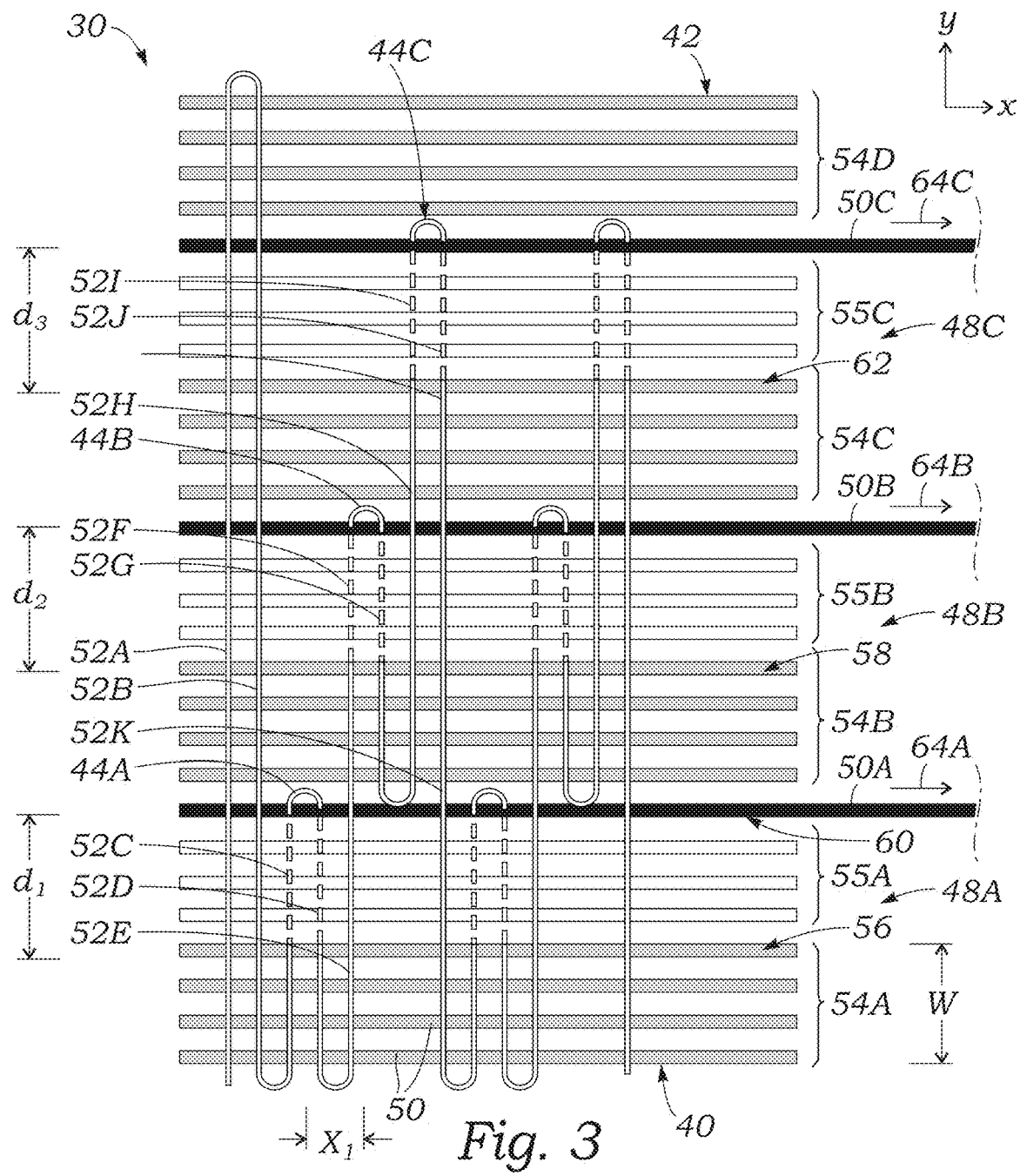
FIG. 3 is a schematic illustration of a representative method of weaving the paravalvular leakage seal of FIG. 1.

FIG. 3 illustrates an exemplary weaving pattern that can be used to produce the skirt 30. With reference to FIG. 3, a first portion 52A of the weft yarn can extend over and under the warp yarns in the fabric from the first edge portion 40 to the second edge portion 42. At the second edge portion 42, the weft yarn 52 doubles back, and a second portion 52B of the weft yarn extends over and under each of the warp yarns in the fabric in a direction back toward the first edge portion 40 in the manner of a plain weave. This can define a side edge of the fabric, and prevent the fabric from unraveling when removed from the loom. At the first edge portion 40, the weft yarn 52 can double back again such that a third portion 52C extends over and under the warp yarns 50 of a first woven portion configured as a fully woven strip 54A of the fabric. In the illustrated configuration, the fabric can include four such woven strips 54A-54D spaced apart from one another between the first and second edge portions 40, 42, and extending parallel to the warp yarns 50. The woven strips 54A-54D can be spaced apart by respective partially or semi-woven portions 55A-55C (also referred to as intermediate sealing portions). In the fully woven strips 54A-54D, every pass of the weft yarn 52 can be incorporated into the weave. In contrast, in the semi-woven portions 55A-55C, only a portion of the passes of the weft yarn are incorporated into the weave. In certain examples, in the woven strips 54A-54D, the warp and weft yarns 50, 52 are woven together in a plain weave (or another suitable weave). In other embodiments, the skirt 30 need not include the woven portion 54D above the last row of loops 44, depending upon the particular application.

Still referring to FIG. 3, at an upper edge 56 of the woven strip 54A, the portion 52C of the weft yarn can exit the weave (e.g., the yarn portion 52C is "dropped" from the weave) and can extend or "float" above the warp yarns 50 of the semi-woven portion 55A for a distance $d_1$. In FIG. 3, portions of the weft yarn 52 that are incorporated into the weave are illustrated in solid lines, and portions of the weft yarn 52 that are not incorporated into the weave (such as portion 52C) are illustrated in dashed lines. The portion 52C can then loop around a removable warp yarn 50A (also referred to as a selvedge yarn), and a fourth portion 52D can extend back toward the first edge portion 40 above the warp yarns and out of the weave. When the weft yarn portion 52D reaches the woven strip 54A, the portion 52D can be reincorporated into the weave such that the warp yarns of the woven strip 54A extend over and under the weft yarn portion 52D.

At the first edge portion 40, the warp yarn 52 can double back again, and a fifth portion 52E can extend in a direction toward the second edge portion 42. The fifth portion 52E can be incorporated into the weave through the semi-woven portion 55A and the woven strip 54B until it reaches an upper edge 58 of the woven strip 54B, at which point a sixth portion 52F can exit, or be "dropped" from, the weave. The sixth portion 52F can extend or float above the warp yarns 50 of the semi-woven portion 55B for a distance $d_2$ in a direction toward the second edge portion 42. The sixth portion 52F can then loop around a removable warp yarn 50B, and a seventh portion 52G of the weft yarn can extend in a direction back toward the first edge portion 40 outside of the weave.

When the seventh portion 52G reaches the upper edge 58 of the woven strip 54B, the seventh portion 52G can be reincorporated into the weave such that the warp yarns of the woven strip 54B extend over and under the seventh portion 52G. When the seventh portion 52G reaches a lower edge portion 60 of the woven strip 54B, the weft yarn can double back, and an eighth portion 52H can extend in a direction toward the second edge portion 42. The eighth portion 52H can be incorporated into the weave through the semi-woven portion 55B and the woven strip 54C until the eighth portion reaches an upper edge portion 62 of the woven strip 54C. At this point, a ninth portion 52I can exit the weave and extend a distance $d_3$ over the warp yarns 50 of the semi-woven portion 55C toward the second edge portion 42. At the woven strip 54D, the ninth portion 52I can loop around a removable warp yarn 50C, and a tenth weft yarn portion 52J can extend back toward the first edge portion 40 outside of the weave.

When the tenth portion 52J reaches the upper edge 62 of the woven strip 54C, the weft yarn can be reincorporated into the weave such that an eleventh weft yarn portion 52K extends back to the first edge portion 40 in the weave. When the portion 52k reaches the first edge portion 40, the weft yarn can double back, and the foregoing pattern can be repeated along a length of the fabric (e.g., to the right in FIG. 3). FIG. 3 illustrates two complete instances of the foregoing weave pattern.

When the weave pattern has been repeated a selected number of times (e.g., to produce a fabric having length corresponding to the circumference of the prosthetic valve), the removable warp yarns 50A-50C can be removed from the weave. For example, in the embodiment illustrated in FIG. 3, the warp yarns 50A-50C can be pulled out of the fabric in the direction of respective arrows 64A-64C. This can cause the portions of the weft yarn 50 that are outside the weave to be released from the fabric, thereby forming the loops 44. For example, when the removable warp yarn 50A is removed from the weave, the portions 52C and 52D of the weft yarn are released from the fabric, and can form a looped filament 44A in extending from the woven strip 54A (e.g., in the manner of terrycloth). Likewise, removing the warp yarn 50B can release the weft yarn portions 52F and 52G such that they form a looped filament 44B extending from the woven strip 54B, and removing the warp yarn 50C can release the weft yarn portions 52I and 52J such that they form a looped filament 44C extending from the woven strip 54C.

Thus, removing the warp yarns 50A-50C results in a plurality of looped filaments 44 arranged in the three rows 48A-48C extending lengthwise along the skirt 30, as described above. FIG. 2 illustrates the skirt 30 with the removable warp yarn 50A removed for purposes of illustration. Returning to FIG. 3, and referring to the Cartesian x- and y-axes for reference, the rows 48A-48C of loops 44 can be offset from each other in a direction along the y-axis (e.g., parallel to the longitudinal axis of the valve) by a distance equal to the length of the loops plus the width of the woven strip 54 from which the loops extend. For example, the first row 48A of loops 44 adjacent the first edge portion 40 is offset from the second row 48B of loops by a distance equal to a width W of the woven strip 54A plus the distance $d_1$, the length of the loops 44.

Meanwhile, although the loops 44 are shown axially aligned in FIG. 1 for purposes of illustration, the loops 44 can also be spaced apart from one another in a direction along the x-axis (e.g., circumferentially around the prosthetic valve when the skirt 30 is secured to the valve). For example, in the embodiment illustrated in FIG. 3, a center or apex of the loop 44B is spaced apart from a center or apex of the loop 44A by a distance $x_1$ corresponding to, for example, the distance along the x-axis occupied by the weft yarn portions 52D and 52E in the weave. Thus, in the illustrated configuration, each loop 44 is offset from the next sequential loop 44 in the neighboring rows in a direction along the x-axis by the distance $x_1$. Thus, the loop 44A is offset from the loop 44B by the distance $x_1$ in the negative x direction, and the loop 44C is offset from the loop 44B by the distance $x_1$ in the positive x direction. Loops 44 in the same row are offset from each other along the x-axis by a distance equal to $3x_1$.

In certain embodiments, when the fabric has been removed from the loom and the removable warp yarns 50A-50C have been removed from the weave, the loops 44 can be shape-set such that they extend out of the plane of the fabric (e.g., transverse to the longitudinal axis of the valve and, thus, to the direction of flow through the valve). For example, referring again to FIG. 1, the loops 44 can be shape-set such that they extend radially outwardly from the surface 46 of the skirt 30 at an angle when the skirt is secured to the frame.

Figure 4:
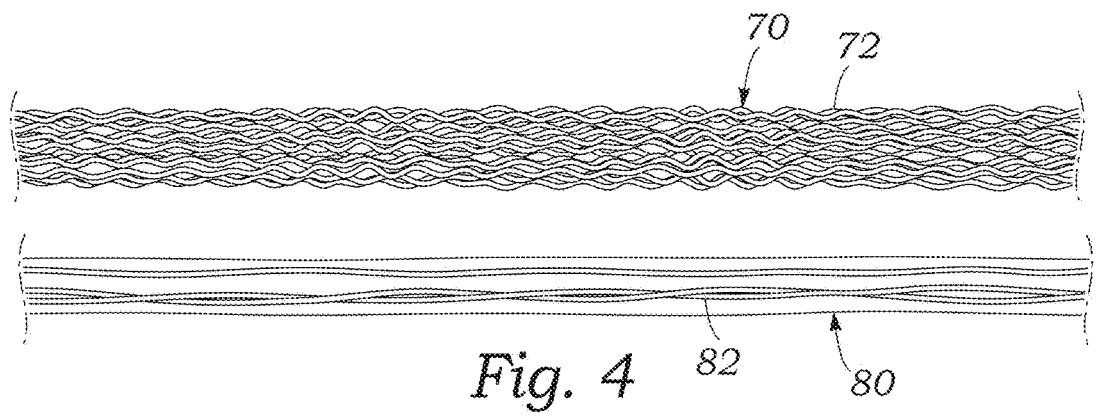
FIG. 4 is a side elevation view illustrating a textured yarn and a fully drawn yarn.

In certain configurations, one or both of the warp and weft yarns 50, 52 can also comprise textured yarns. A representative example is illustrated in FIG. 4, which shows an exemplary textured yarn 70 and a fully drawn yarn 80. The textured yarn 70 includes a plurality of constituent fibers 72 that have been crimped, coiled, crinkled, looped, etc., such that the fibers are not as tightly bundled as the fibers 82 of the fully drawn yarn 80. This can increase the surface area of the textured yarn 70, which can improve the blood clotting properties of the yarn, as further described below. Additionally, the fibers 72 from which the yarns 50, 52 are formed can be sized to promote a biological response or interaction at the cellular level between the yarns 50, 52 and the blood flowing past the skirt.

For example, blood cells typically range in size from 2 μm to 15 μm. For example, the diameter of red blood cells typically ranges from 6 μm to 8 μm, and the diameter of platelets typically ranges from 2 μm to 3 μm. Thus, utilizing fibers 72 having a diameter sized to approximately match the diameter of blood cells (e.g., 1 μm to 20 μm) can promote interaction between the fibers and blood cells at the cellular level. For example, the fibers 72 can be configured to promote thrombus formation along the skirt 30, and along the looped filaments 44 in particular, thereby improving the sealing characteristics of the skirt.

In certain configurations, the warp and weft yarns can comprise a variety of biocompatible materials, such as natural fibers (e.g., silk, cotton, etc.), synthetic polymeric materials (e.g., polyethylene terephthalate (PET), Nylon, polytetrafluoroethylene (PTFE), etc.), or metals (e.g., Nitinol, gold, etc.). In other embodiments, the skirt 30 need not comprise a woven fabric, but can comprise a thin polymeric film or laminate with which the looped filaments are integrally formed, or to which the looped filaments are attached.

The skirt 30 can provide a number of significant advantages over known skirt embodiments. For example, the loops 44 can obstruct the flow of blood past the valve, reducing the velocity and volume of blood that leaks past the valve after implantation. The flow obstruction provided by the loops 44 can increase the dwell time of blood near the skirt. This, together with the fiber diameters described above, can induce thrombus formation and promote sealing between the skirt and the surrounding tissue.

Additionally, the loops 44 can be flexible, allowing the loops to conform to the shape of the surrounding anatomy. Because the loops 44 extend radially outwardly from the surface of the skirt 30, the free end portions of the loops can also extend into folds and crevices in the surrounding anatomy to promote a more complete seal. Moreover, when the prosthetic valve is implanted in the native aortic valve, blood around the exterior of the valve can apply force to the loops 44 during ventricular diastole in a direction that is opposite to the direction of blood flow through the valve. This can enhance the bending of the loops 44 away from the skirt 30, further enhancing the sealing properties. Additionally, by extending outwardly from the exterior of the valve, the loops 44 can also block thrombi from moving past the valve, reducing the likelihood of stroke.

Figure 5:
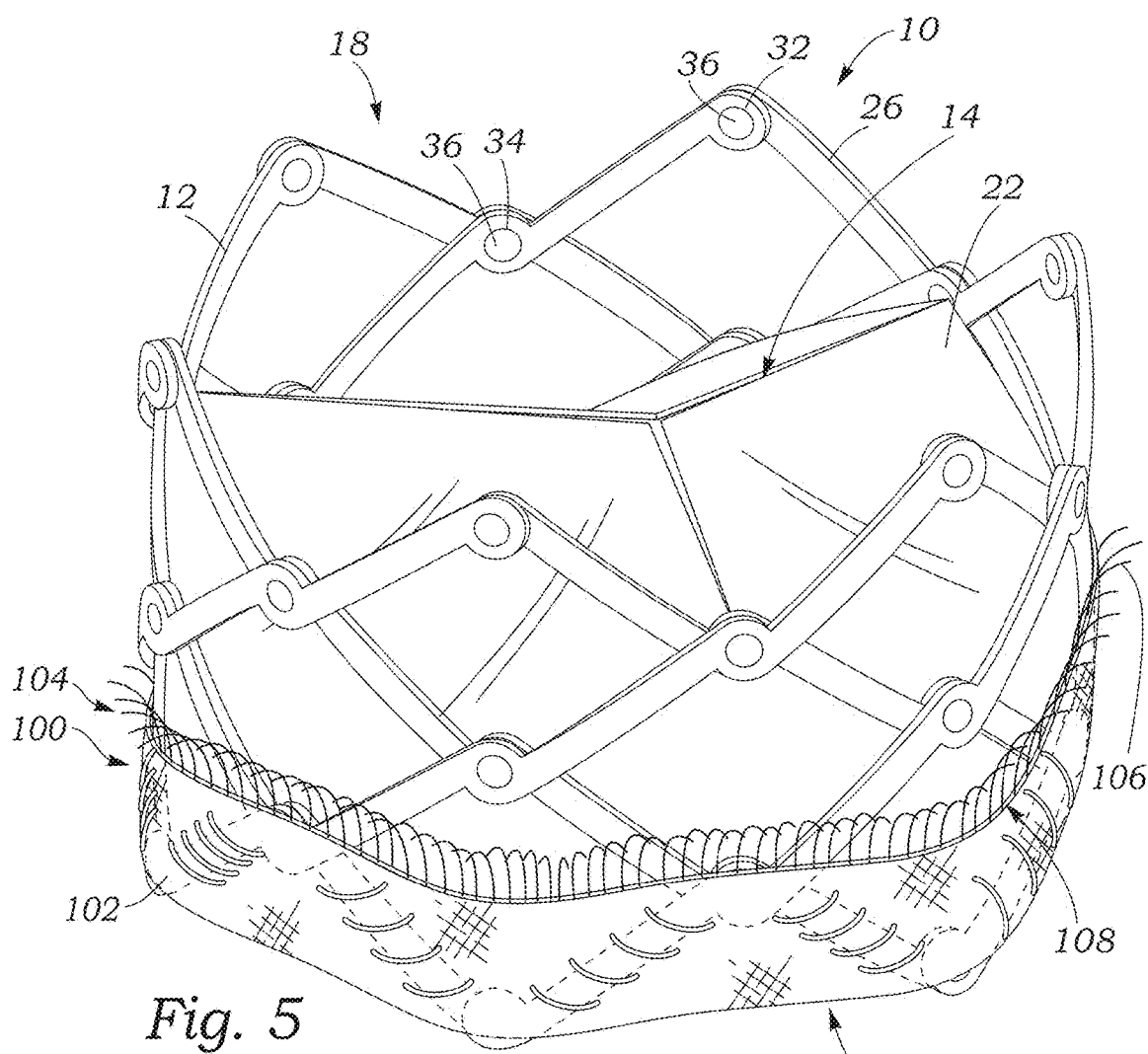
FIG. 5 is a perspective view illustrating a prosthetic heart valve including another embodiment of a paravalvular leakage seal including a woven portion and a plurality of filaments extending from the woven portion.

FIG. 5 illustrates a prosthetic valve 10 including another embodiment of a sealing member or skirt 100. In the illustrated embodiment, the skirt 100 can comprise a woven portion configured as a fabric strip 102, and a fringe portion 104 comprising a plurality of filaments configured as yarns 106 extending from an edge portion 108 of the fabric strip 102. In certain examples, the yarns 106 can be warp yarns extending from the weave of the fabric strip 102 which are not interwoven with any weft yarns, or vice versa. In some embodiments, the yarns 106 can be frayed yarns. For example, the yarns 106 can comprise a plurality of fibers or threads spun together.

Figure 6:
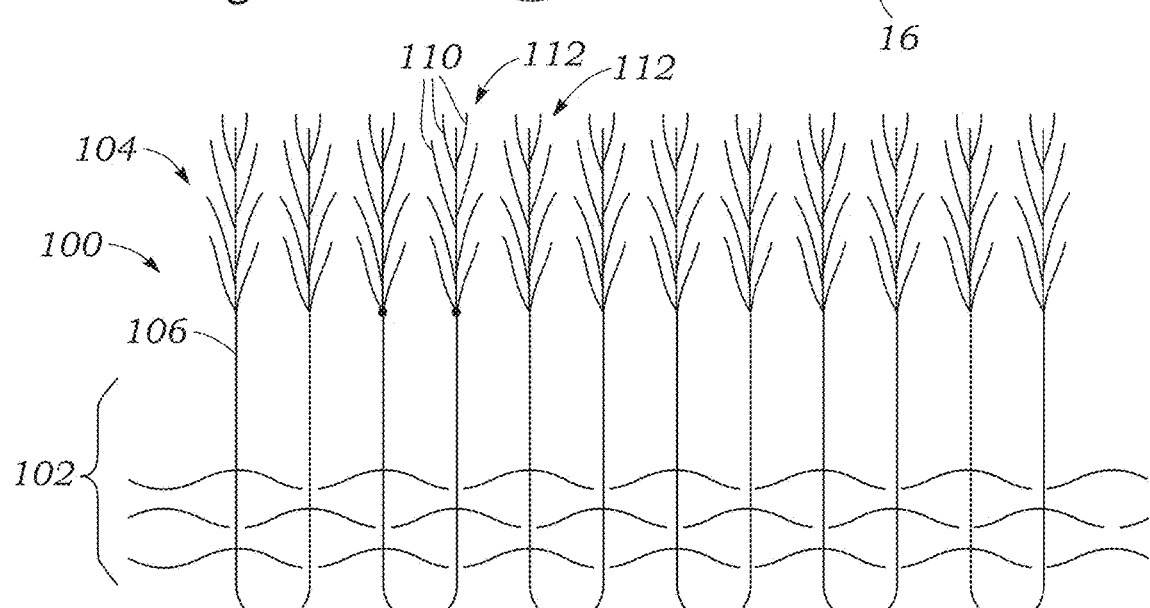
FIG. 6 is a schematic illustration of the paravalvular leakage seal of FIG. 5.

FIG. 6 schematically illustrates a portion of such a skirt 100 in greater detail. In the configuration illustrated in FIG. 6, the yarns 106 can be frayed such that the constituent fibers 110 of the yarns are separated from one another and form fan-like structures 112. For example, in some embodiments, the fibers 110 of the yarns 106 can have diameters of 1 μm to 20 μm, a size at which electro-static forces between the fibers can dominate gravitational forces, causing the fibers to splay apart. This can increase the surface area of the yarns 106, which can promote a biological response at the cellular level between blood and the fibers 110 of the skirt, as described above with respect to the embodiment of FIG. 1. Thus, the fibers 110 can be configured to promote thrombus formation along the fringe portion 104, thereby improving the sealing characteristics of the skirt 100.

In certain embodiments, the yarns 106 can comprise any of a variety of hydrophobic surface treatments or coatings in order to promote separation of the fibers 110 and increase the surface area of the fringed portion 104. In other embodiments, the yarns 106 can comprise hydrophilic surface treatments, such as polyethylene glycol (PEG), or other coatings that covalently bond to the fibers. The yarns 106 can also comprise coatings or treatments to promote a biological response (e.g., thrombus formation) from blood in contact with the yarns, and/or lubricious coatings such as Serene™ lubricious coatings available from Surmodics, Inc. In other embodiments, an electrostatic charge can be applied to the yarns 106 such that the fibers 110 repel each other to increase the separation of the fibers. In still other embodiments, the fibers 110 can be textured fibers, as described above with respect to the embodiment of FIG. 1, or coated or felted with short-length, small diameter fibers. In other examples, the yarns 106 can also form loops.

Figure 7:
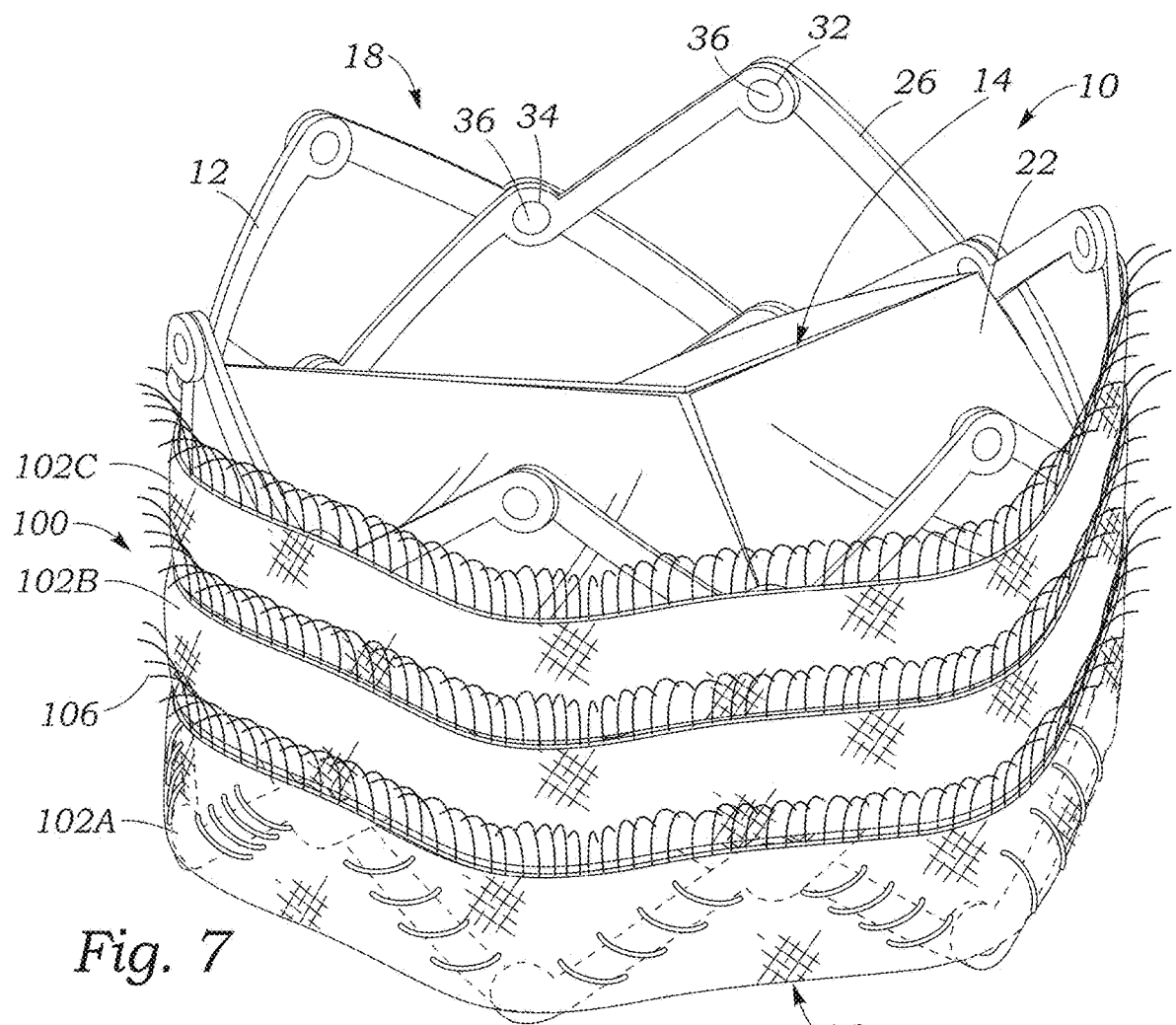
FIG. 7 is a perspective view of the prosthetic heart valve of FIG. 5 including another embodiment of the paravalvular leakage seal including a plurality of woven portions arranged in a tiered arrangement on the outside of the valve.

With reference to FIG. 7, in another configuration, the skirt 100 can comprise multiple fabric strips 102 arranged one on top of the other in a tiered arrangement. For example, in the illustrated embodiment, the skirt 100 can comprise three fabric strips 102A-102C arranged such that the frayed edge portion 108 of each strip is oriented toward the outflow end 18 of the frame. Although the illustrated embodiment includes three fabric strips 102A-102C, the skirt 100 can comprise any suitable number of fabric strips 102 depending upon, for example, the width of the fabric strips, the length of the prosthetic valve, etc. In other embodiments, both longitudinal edges of the fabric strips 102 can comprise yarns 106.

Figure 8:
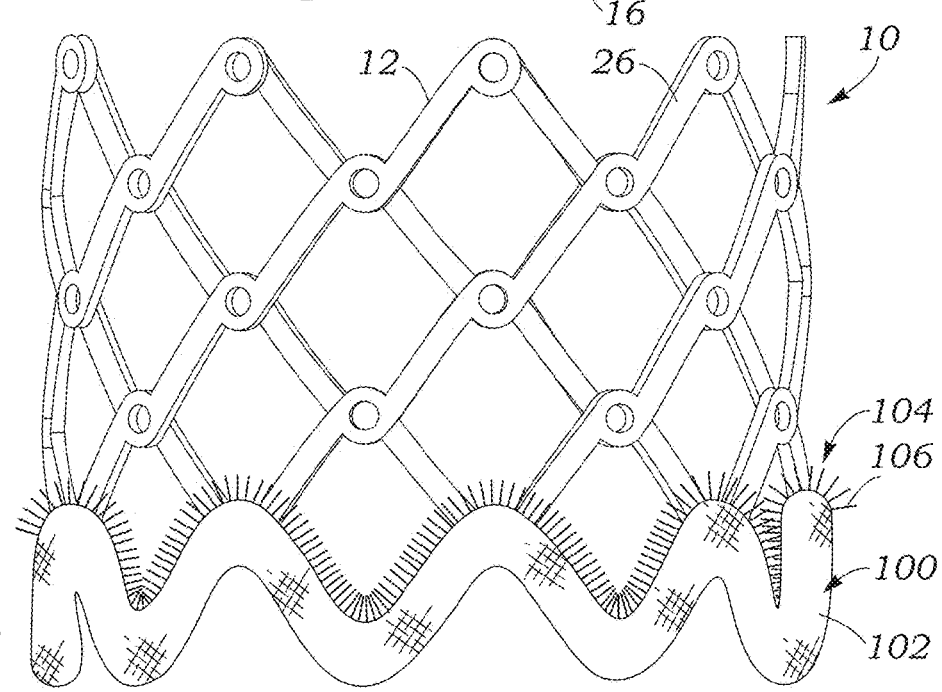
FIG. 8 is a side elevation view of the prosthetic heart valve of FIG. 5 including another embodiment of the paravalvular leakage seal in which the woven portion extends in a zig-zag pattern around the valve parallel to the strut members of the frame.

In another configuration illustrated in FIG. 8, the skirt 100 can be secured to the struts 26 such that it extends along the struts and forms a zig-zag shape. Multiple skirts 100 can be secured to the strut members 26 of the frame in this fashion, depending upon the particular application.

Figure 9:
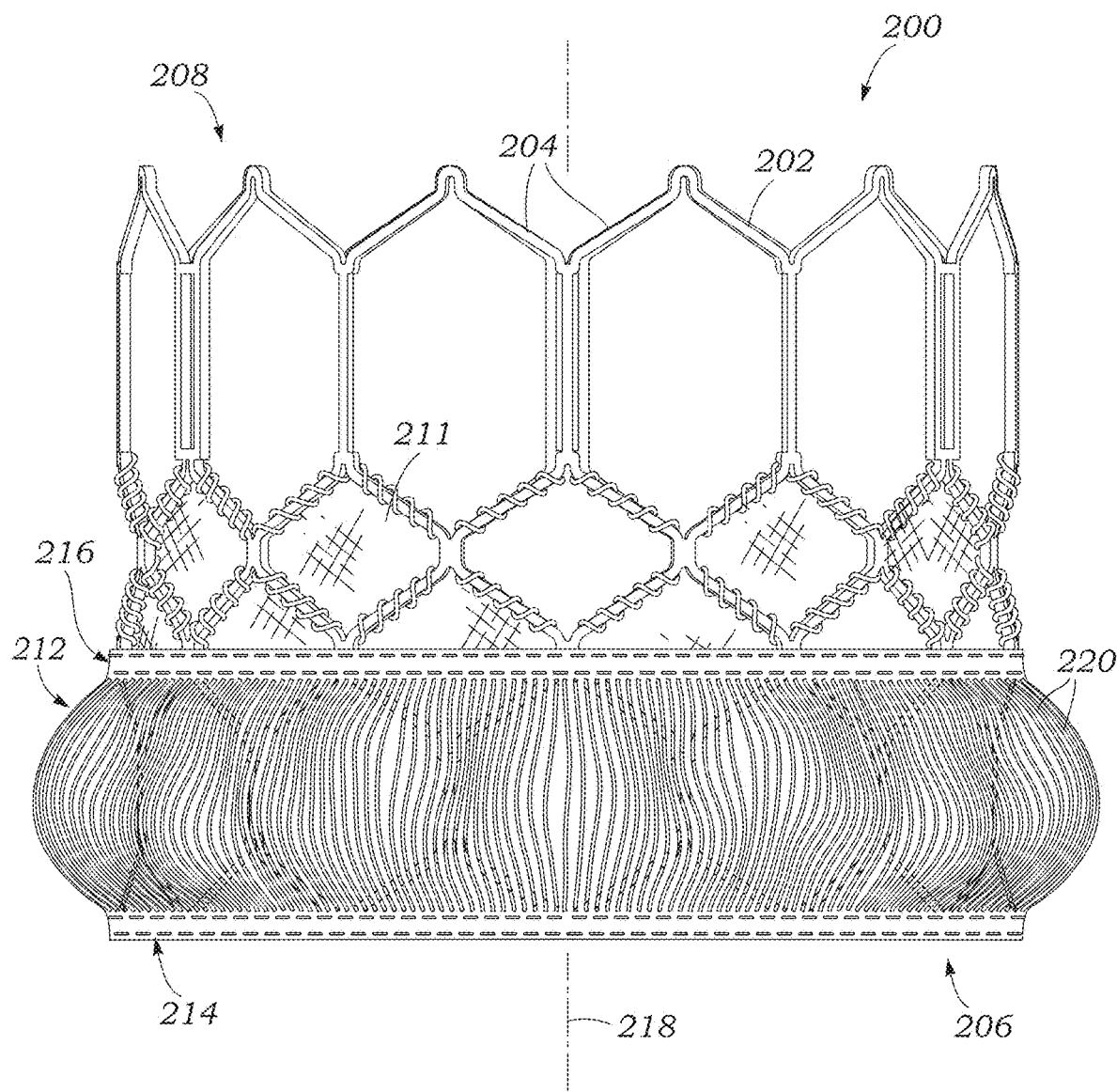
FIG. 9 is a perspective view of another embodiment of a prosthetic heart valve including a paravalvular leakage seal having a first woven portion, a second woven portion, and a plurality of yarns that extend between the first and second woven portions to form loops.

FIG. 9 illustrates another embodiment of a prosthetic valve 200 configured as the Edwards Lifesciences Corporation SAPIEN® 3 prosthetic heart valve described in detail in U.S. Pat. No. 9,393,110, which is incorporated herein by reference. The prosthetic valve 200 includes a radially expandable and collapsible frame 202 formed by a plurality of angled strut members 204, and having an inflow end 206 and an outflow end 208. Although not shown, the prosthetic valve 200 can also include a leaflet structure comprising two leaflets, three leaflets, or any other suitable number of leaflets situated within and secured to the frame as described in U.S. Pat. No. 9,393,110.

The prosthetic valve 200 can comprise an inner skirt 211 secured to an interior surface of the frame, and an outer sealing element configured as a skirt 212 disposed around the exterior of the frame 202. In the illustrated configuration, the skirt 212 can comprise a first circumferentially-extending portion 214 situated adjacent the inflow end 206 of the frame and a second circumferentially-extending portion 216. The circumferential portions 214, 216 can be spaced apart from each other along a longitudinal axis 218 of the frame, and coupled together by a plurality of filaments 220. The filaments 220 can extend longitudinally along the outside of the frame between the portions 214, 216, and can curve outwardly from the frame when the frame is in the expanded configuration to form loops. The looped filaments 220 can be configured to promote sealing by obstructing blood flow past the skirt and increasing the dwell time of blood in the vicinity of the filaments, as described above.

In certain configurations, the circumferential portions 214, 216 can be configured as one or more strips of woven fabric. The filaments 220 can be yarns that are incorporated into the fabric of the portions 214 and 216, and extend axially therebetween. The skirt 212 illustrated in FIG. 9 includes a single layer of looped filaments 220 for ease of illustration, although the skirt embodiments described herein can include two or more layers of looped filaments, depending upon the number of fabric strips incorporated into the portions 214, 216. Increasing the number of looped filaments (e.g., by increasing the number of fabric strips) can increase the overall surface area of the sealing element available for thrombogenesis.

For example, FIG. 10 illustrates a representative embodiment of a skirt 212 configured to provide two layers of looped filaments 220 when secured to the frame, and laid out flat for purposes of illustration. The skirt 212 can comprise a main body 224 including a first fabric strip 226A, a second fabric strip 226B, and a third fabric strip 226C. The fabric strip 226B can be located between the fabric strips 226A and 226C. The fabric strip 226B can be spaced apart from the fabric strip 226A by a floating yarn portion 228A comprising a plurality of filaments or yarns 220. Likewise, the fabric strip 226C can be spaced apart from the fabric strip 226B by a floating yarn portion 228B comprising a plurality of yarns 220.

In the illustrated configuration, the first fabric strip 226A can comprise warp and weft yarns woven together. At an edge portion 230 of the fabric strip 226A, the yarns 220 can exit the weave and extend or "float" to the second fabric strip 226B to form the floating yarn portion 228A. When the floating yarns 220 reach the second fabric strip 226B, the yarns can be reincorporated into the woven fabric of the strip 226B. At an edge portion 232 of the fabric strip 226B, the yarns 220 can exit the weave again, and extend or float from the strip 226B to the strip 226C to form the floating yarn portion 228B. When the floating yarns 220 reach the fabric strip 226C, they can be reincorporated into the weave of the fabric strip 226C. In certain configurations, the yarns 220 are warp yarns, although the yarns 220 may also be weft yarns, or a combination of warp and weft yarns, depending upon the particular application.

Referring to FIG. 11, the main body 224 of the skirt 212 can be folded about the fabric strip 226B such that the fabric strip 226C is adjacent the fabric strip 226A, and such that the floating yarn portions 228A and 228B are overlaid or coextensive with each other. The folded skirt 212 can then be secured to the frame (e.g., by suturing) such that the fabric strips 226A, 226C form the first portion 214, and the fabric strip 226B forms the second portion 216. In this manner, the longitudinally-extending yarns 220 of the floating yarn portion 228A form a first or radially inward layer of curved yarns or loops, and the longitudinally-extending yarns 220 of the floating yarn portion 228B form a second or radially outward layer of curved yarns or loops (or vice versa). To produce the single layer of looped filaments 220 illustrated in FIG. 9, the skirt 212 need only include, for example, the woven strips 226A and 226B, and the floating yarn portion 228A.

Referring to FIGS. 12A and 12B, which illustrate a portion of the frame 202, the strut members 204 can be arranged end-to-end to form a plurality of rows or rungs of strut members that extend circumferentially around the frame 202. For example, the frame 202 can comprise a first or lower row I of angled strut members forming the inflow end 206 of the frame; a second row II of strut members above the first row; a third row III of strut members above the second row; a fourth row IV of strut members above the third row, and a fifth row V of strut members above the fourth row and forming the outflow end 208 of the frame. The structure and characteristics of the rows I-V of strut members 204 are described in greater detail in U.S. Pat. No. 9,393,110, incorporated by reference above. The strut members 204 of the frame 202 can also be grouped into columns. For example, the frame 202 can include a plurality of first or "type A" columns, and second or "type B" columns arranged alternatingly around the circumference of the frame. In the illustrated configuration, the type A columns comprise the strut members 204 on the left side of the diamond-shaped windows 205 defined by the rows IV and V of strut members, and the strut members extending downwardly therefrom. The type B columns comprise the strut members 204 on the right side of the windows 205, and the strut members extending downwardly therefrom.

With reference to FIGS. 9 and 12A, the first portion 214 of the skirt 212 can be secured (e.g., by suturing) to the first row I of strut members 204 adjacent the outflow end of the frame. The second portion 216 can be secured along the intersection of the second and third rows II and III of struts 204. A length of the yarns 220 can be configured such that the yarns curve radially outwardly from the surface of the frame 202 when the frame is in the expanded configuration and form loops. For example, when coupled to the frame, the skirt 30 can have a length L corresponding approximately to the sum of the lengths of strut members 204A, 204B, and 204C identified in FIG. 12A. In this manner, when the frame 202 is in the radially compressed or crimped configuration (in which the strut members 204A, 204B, and 204C are axially aligned or nearly aligned with one another), the yarns 220 can be pulled straight to reduce the crimp profile of the valve for insertion into a delivery sheath.

Figure 13:
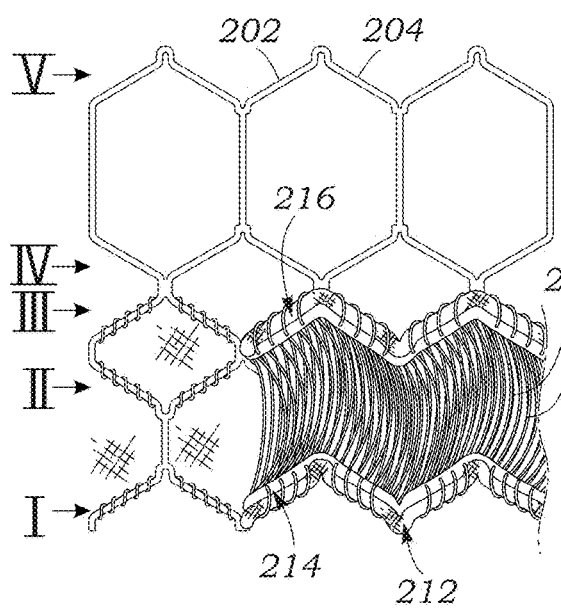
FIG. 13 is a side elevation view illustrating a portion of the frame of the prosthetic valve of FIG. 9 with the first woven portion of the paravalvular leakage seal coupled to a first rung of frame struts, and the second woven portion coupled to a third rung of frame struts.

In the configuration illustrated in FIGS. 9-12B, the portions 214, 216 of the skirt 212 extend generally parallel to each other and are not angled with respect to the longitudinal axis 218 of the frame. In other configurations, one or both of the portions 214, 216 can be attached to the frame such that they are angled relative to the longitudinal axis 218 of the frame. For example, FIG. 13 illustrates a configuration in which the portion 214 is secured to the first row I of strut members such that the portion 214 extends parallel to the angled strut members 204 around the circumference of the frame 202. In other words, the portion 214 forms a zig-zag pattern along the first row I of strut members 204 that corresponds to the zig-zag pattern of the strut members of the first row I. The portion 216 is secured to the third row III of strut members 204, and also extends parallel to the angled strut members of the third row III.

In embodiments in which the portions 214, 216 of the skirt 212 extend parallel to the strut members 204 of the respective row to which they are secured, the skirt 212 can extend between even-numbered rows of strut members, odd-numbered rows of strut members, or from an odd-numbered row to an even-numbered row, or vice versa. For example, in the configuration illustrated in FIG. 13, the first portion 214 is secured to the first row I, and the second portion 216 is secured to the third row III such that the skirt extends between two odd-numbered rows of strut members. With respect to the frame 202 illustrated in FIGS. 9-15, where the skirt extends from an odd-numbered row to another odd-numbered row (e.g., from row I to row III), or from an even-numbered row to another even-numbered row (e.g., from row II to row IV), the portions 214, 216 can be arranged such that the yarns 220 extend in a direction parallel to the longitudinal axis 218 of the frame. Stated differently, where the skirt 212 extends between odd-numbered rows or between even-numbered rows, a given yarn 220 can extend from a location along the first portion 214 that is secured to a type A column to a location along the second portion 216 that is also secured to a type A column.

Figure 14:
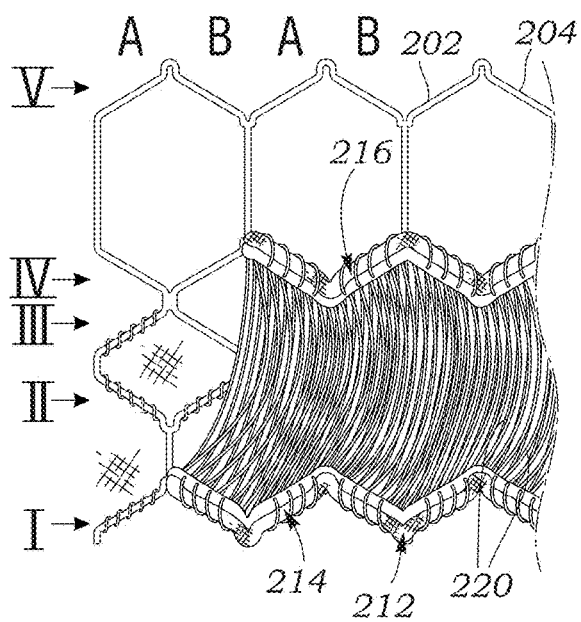
FIG. 14 is a side elevation view illustrating a portion of the frame of the prosthetic valve of FIG. 9 with the first woven portion of the paravalvular leakage seal coupled to a first rung of frame struts, and the second woven portion coupled to a fourth rung of frame struts.

In configurations in which the skirt extends from an odd-numbered row to an even-numbered row (or vice versa), the portions 214, 216 can be circumferentially offset from each other such that the yarns 220 extend at an angle to the longitudinal axis 218. For example, with reference to FIG. 14, the first portion 214 is coupled to the first row I of strut members, and the second portion 216 is coupled to the fourth row IV of the strut members. As illustrated in FIG. 14, the first and second portions 214, 216 of the skirt are offset from each other about the circumference of the frame such that a given yarn 220 that extends from a location along the first portion 214 that is secured to a type A column of strut members is coupled to a location along the second portion 216 that is secured to a type B column of strut members. This allows the yarns 220 to extend parallel to the longitudinal axis of the frame when the frame is crimped.

Figure 15:
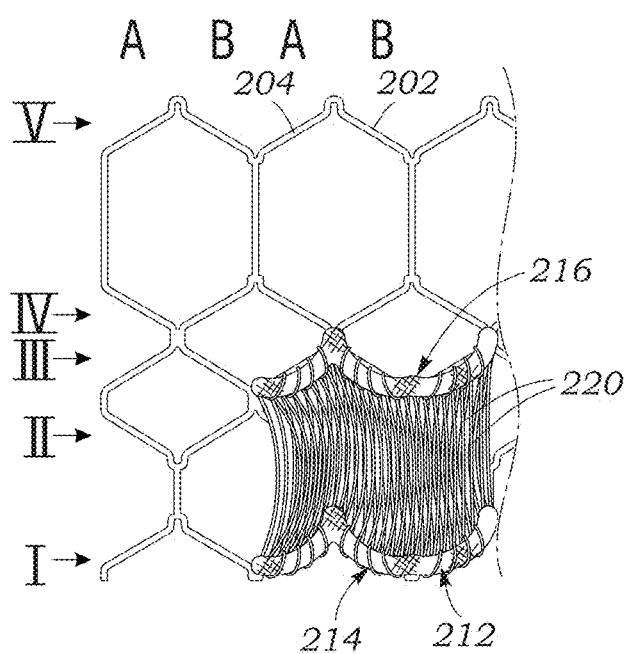
FIG. 15 is a side elevation view illustrating a portion of the frame of the prosthetic valve of FIG. 9 with the paravalvular leakage seal draped along the struts of the frame.

FIG. 15 illustrates another configuration in which the skirt 212 is draped between intersections or apices 234 of the strut members 204 such that the portions 214, 216 hang from the frame 202. For example, in the illustrated configuration the portion 214 is secured to intersections of strut members of row I, and the portion 216 is secured to intersections of the strut members of rows III and IV. One or both of the portions 214, 216 can be secured in this manner, depending upon the particular characteristics desired.

In certain examples, the skirt 212 can comprise twisted yarns, or non-twisted yarns. The skirt 212 can also comprise core-spun yarns, in which wrapper fibers are spun around a core yarn. The wrapper fibers may be wispy or diffuse in order to increase the surface area of the core-spun yarn to promote a biological response, as described above. In certain embodiments, the skirt 212 can also include loops similar to the loops 44 of FIG. 1, in addition to the floating yarn portions 228.

Figures 16A, 16B:
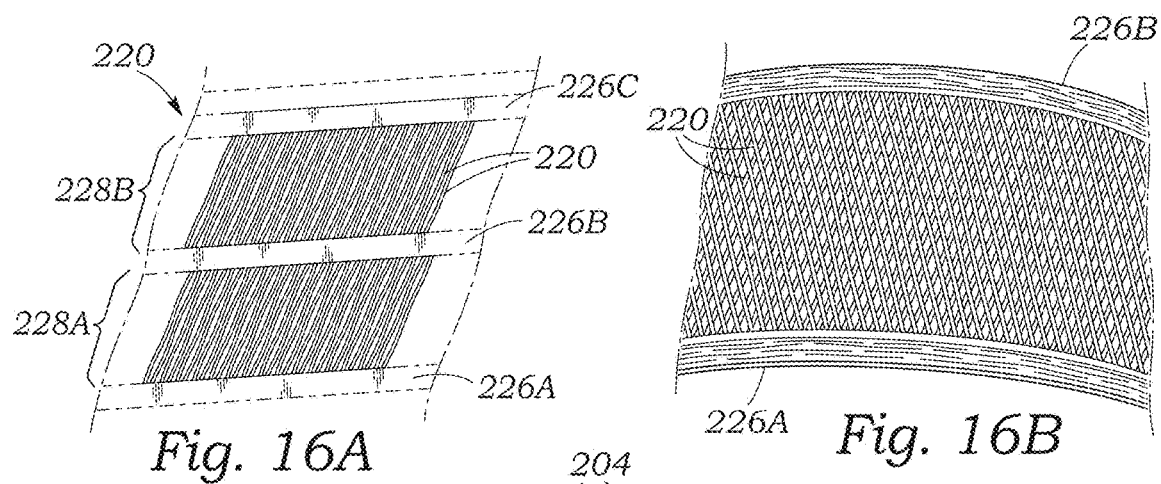
FIGS. 16A and 16B illustrate another embodiment of the paravalvular leakage seal of FIG. 9 in which the longitudinally-extending yarns extend at an angle between the first and second woven portions of the seal.

FIGS. 16A and 16B illustrate another skirt 212 in which the yarns 220 extend between the fabric strips 226A, 226B, and 226C at an angle. For example, referring to FIG. 16A, the yarns 220 of the floating yarn portion 228A extend at an angle to the fabric strips 226A and 226B. The yarns 220 of the floating yarn portion 228B can also extend at an angle to the fabric strips 226B and 226C. In this manner, when the main body 224 is folded, the yarns 220 of the floating yarn portion 228A can be at an angle to or "criss-crossed" with the yarns of the floating yarn portion 228B to form a mesh or web as shown in FIG. 16B. In some embodiments, the yarns can extend at an angle of from 10 degrees to 40 degrees. In certain configurations, having the yarns of the floating yarn portions 228A and 228B cross each other at an angle can reduce the potential for gaps between the yarns resulting from the yarns clustering together. In some embodiments, the yarns of the floating yarn portion 228A and the floating yarn portion 228B can be parallel to each other.

Figure 17:
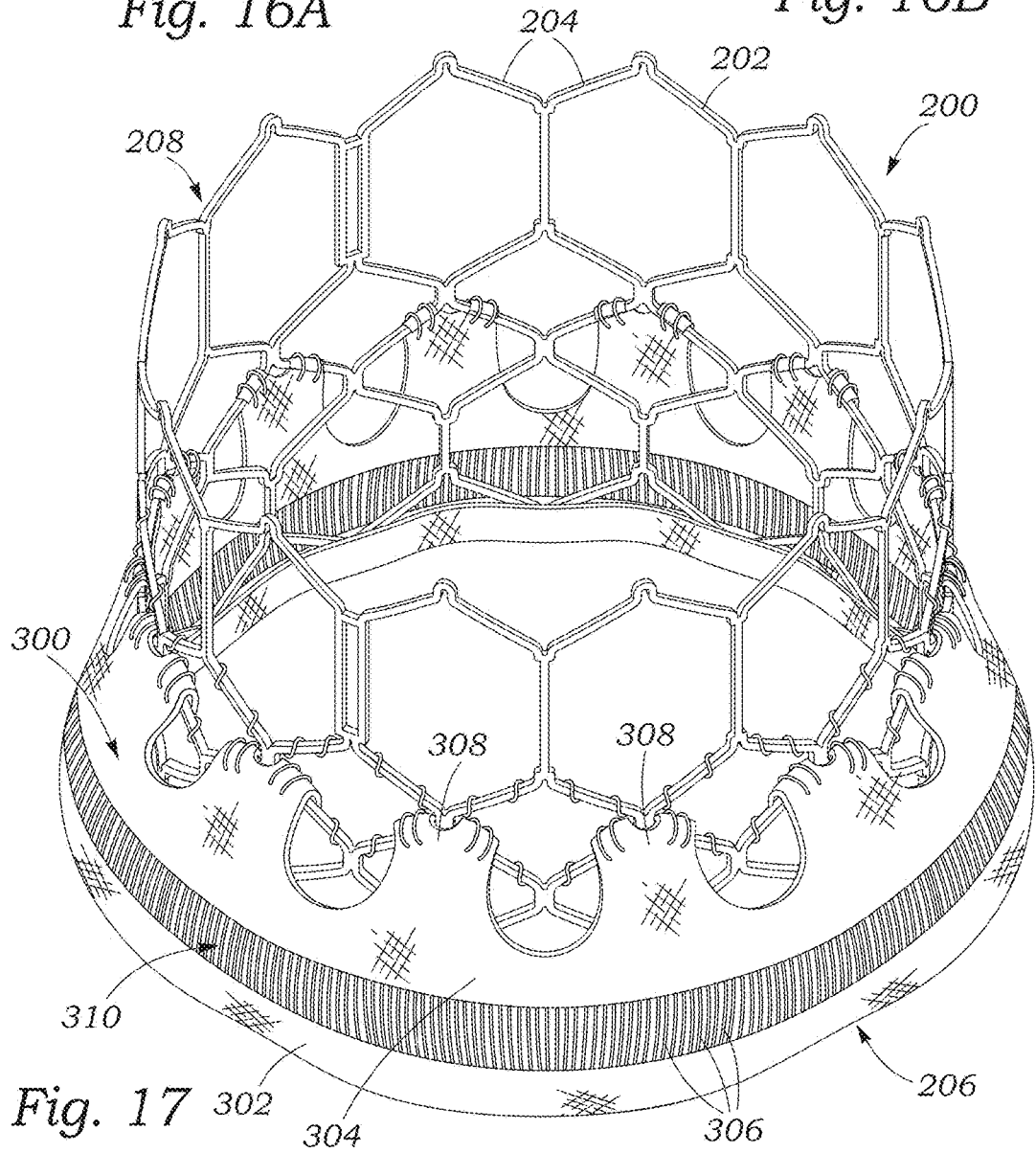
FIG. 17 is a perspective view of the prosthetic heart valve of FIG. 9 including another embodiment of the paravalvular leakage seal including a single layer of longitudinally-extending yarns.

FIG. 17 illustrates the prosthetic valve 200 and frame 202 of FIG. 9 including another embodiment of a skirt 300. The skirt 300 can comprise first and second circumferentially-extending portions 302, 304 spaced apart from each other and coupled together by a plurality of filaments configured as yarns 306 extending longitudinally along the frame, similar to the skirt 212. In the embodiment illustrated in FIG. 17, the portions 302, 304 can be relatively wider than the portions 214, 216 of the skirt 212, such that edge portions of the portions 302, 304 curve outwardly from the frame 202 in the expanded configuration, along with the filaments 306. The second portion 304 can also include a plurality of connection portions 308 extending upwardly (e.g., toward the outflow end 208 of the frame) from the portion 304 and secured to the struts 204 (e.g., by suturing).

Figure 18:
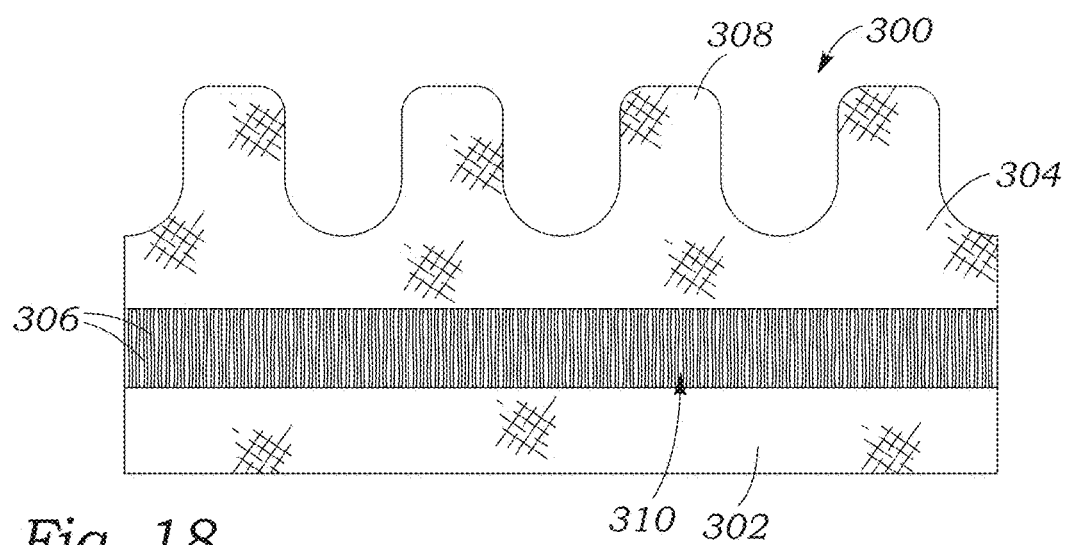
FIG. 18 is a top plan view of a portion of the paravalvular leakage seal of FIG. 17.

In the illustrated configuration, the skirt 300 includes a single layer of longitudinally-extending yarns 306. FIG. 18 illustrates a representative configuration of the skirt 300 laid flat before the skirt is attached to the frame. The first and second portions 302, 304 can comprise woven fabric strips, similar to the skirt 212. The fabric portions 302, 304 can be spaced apart by a floating yarn portion 310 through which the yarns 306 extend. In some embodiments, the yarns 306 can be warp yarns, and the floating yarn portion 310 can be formed by omitting the weft yarns from the floating yarn portion, or by removing selected weft yarns from the weave.

Figure 19:
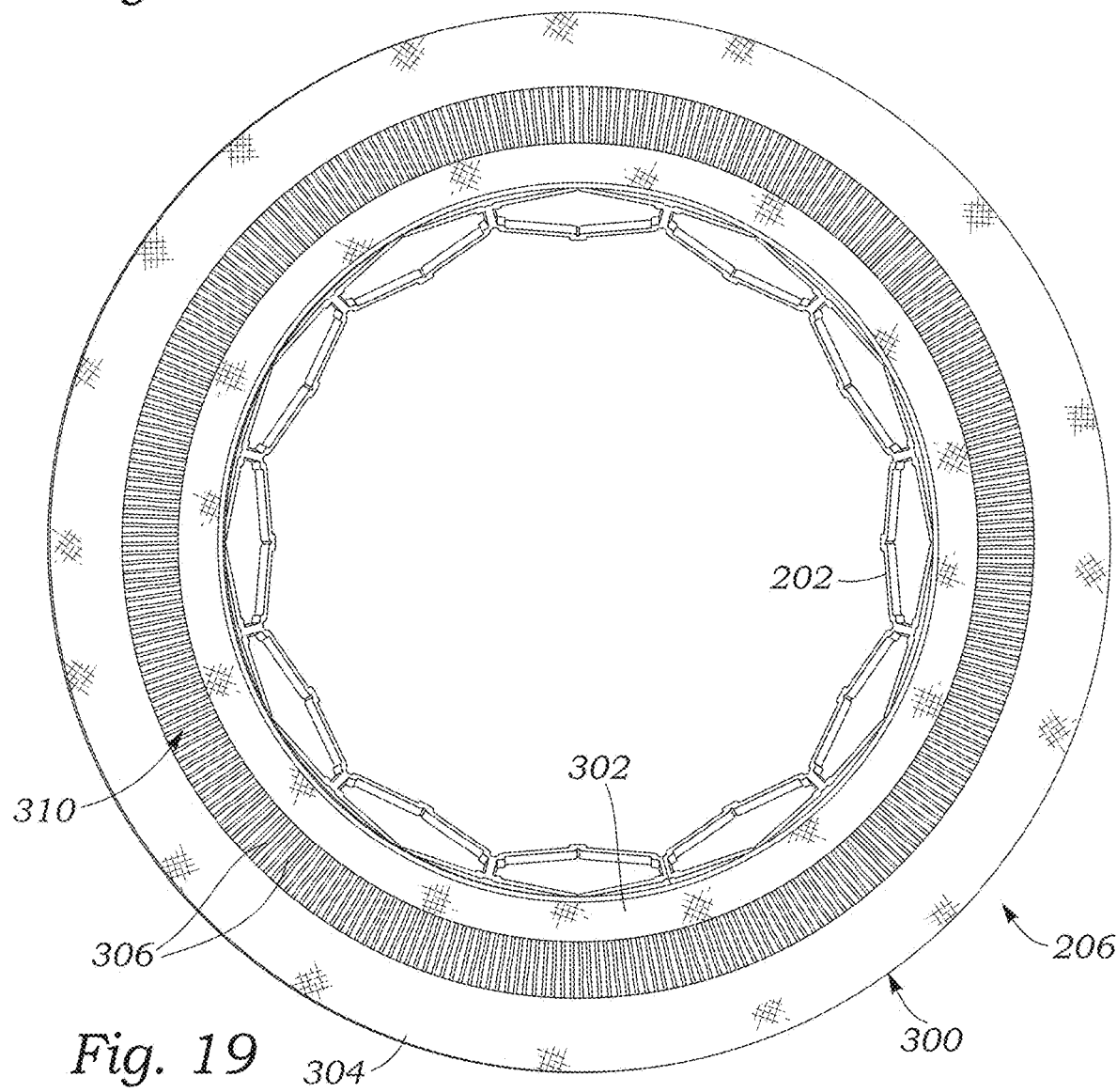
FIG. 19 is a bottom plan view of the prosthetic heart valve of FIG. 17.

When the skirt 300 is secured to the frame, the first portion 302 can be folded around the inflow end portion 206 of the frame 202 such that the first portion is partially disposed within the frame. After implantation, blood can flow through the floating yarn portion 310 and drain from the skirt. In certain configurations, the skirt 300 can have a reduced crimp profile because the skirt is not folded before it is secured to the frame. In other configurations, the portions 302, 304 can be sized such that the floating yarn portion 310 is located on a lower or distal aspect of the skirt when the frame is expanded. For example, FIG. 19 is a perspective view of the distal or inflow end portion of the frame 202 illustrating the yarns 306 located distally of the inflow end portion 206.

Figure 20:
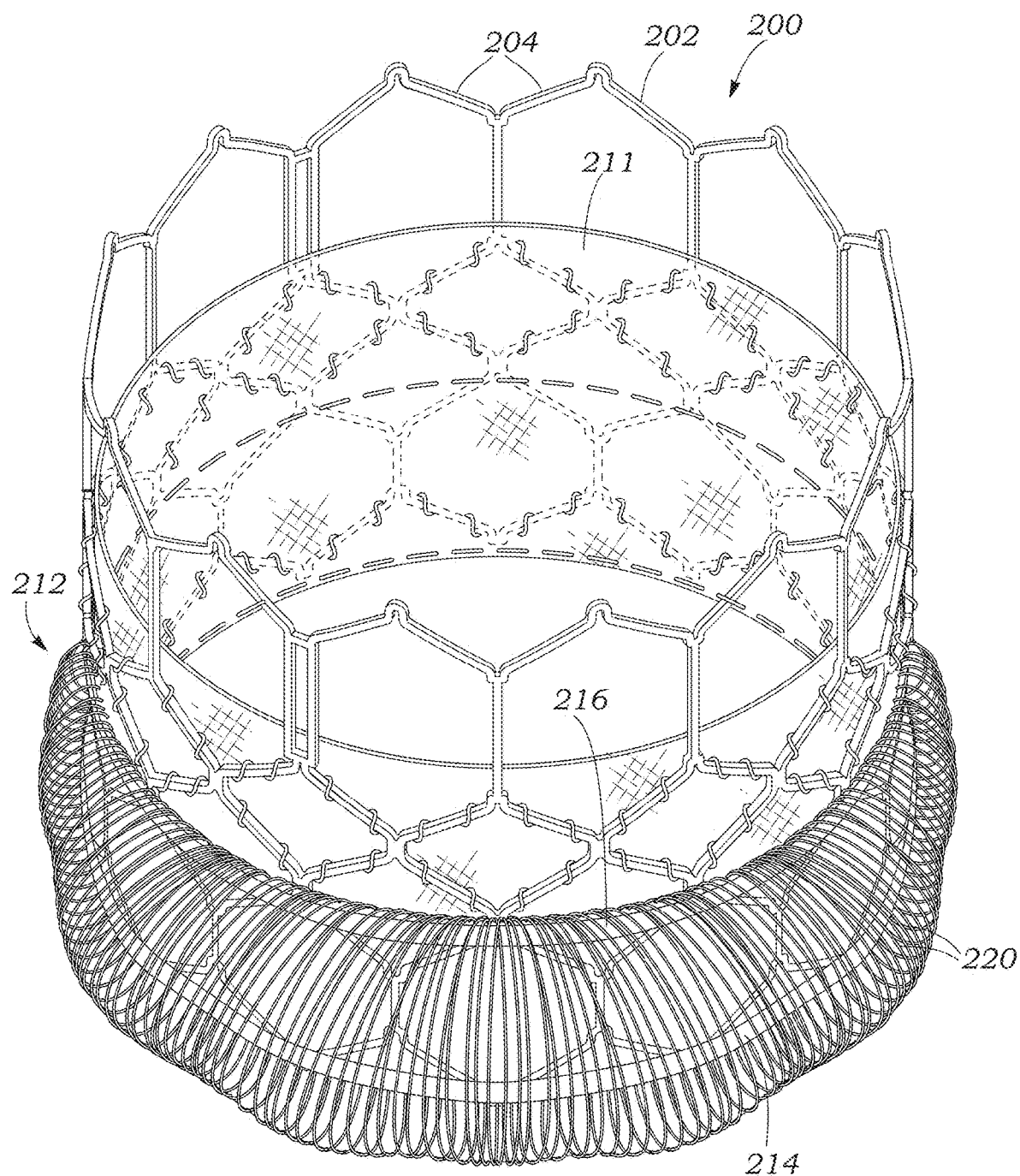
FIG. 20 is a perspective view of the prosthetic heart valve of FIG. 9 including another embodiment of a paravalvular leakage seal.

FIG. 20 illustrates another configuration of the skirt 212 in which the yarns 220 are configured to curve over or around the portions 214, 216 before being reincorporated into the weave. For example, referring to FIGS. 10 and 20, the skirt 212 can be secured to the frame such that the yarns 220 extend from the distal edge portion of the fabric strip 226A, double back and extend proximally and over the fabric strip 226B to the proximal edge portion of the strip 226B such that the yarns form a C-shaped arc. In other embodiments, one or both of the fabric strips 226A, 226B can be omitted, and the yarns 220 can be secured to the frame by being looped through the strut members 204.

Figure 21:
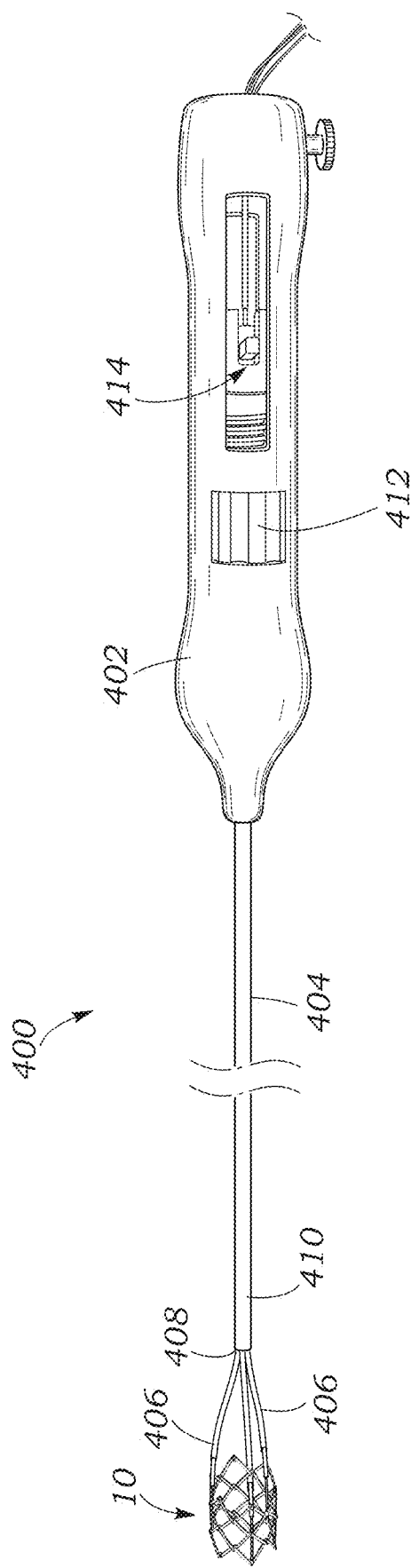
FIG. 21 is a perspective view of a representative embodiment of a delivery apparatus.

The disclosed prosthetic valve embodiments can be radially collapsed and delivered to the heart percutaneously using any of a variety of catheter-based delivery systems. For example, FIG. 21 shows a representative example of a delivery assembly 400 configured for use with the prosthetic valve 10 of FIGS. 1-8 and described in detail in U.S. Publication No. 2018/0153689 incorporated by reference above. The delivery assembly 400 can include a handle 402, an elongate shaft 404 extending distally from the handle 402, and a plurality of actuation members 406 (e.g., in the form of positioning tubes) extending through the shaft and distally outwardly from a distal end 408 of the shaft 404. The actuation members 406 can be coupled to select apices of the valve frame 12.

Initially, the prosthetic valve 10 can be in a radially collapsed configuration within a sheath 410 of the shaft 404. When the distal end of the delivery apparatus has been advanced through the patient's vasculature to the treatment site, the prosthetic valve 10 can be advanced from the sheath 410 using a rotatable actuator 412 on the handle 402. The prosthetic valve 10 can then be positioned at the treatment site, expanded, and deployed using a release assembly generally indicated at 414. Other delivery systems that can be used in combination with the prosthetic valve embodiments described herein can be found in US Patent Application Publication No. 2017/0065415 and US Patent Application Publication No. 2013/0030519, which are incorporated herein by reference.

Figure 22:
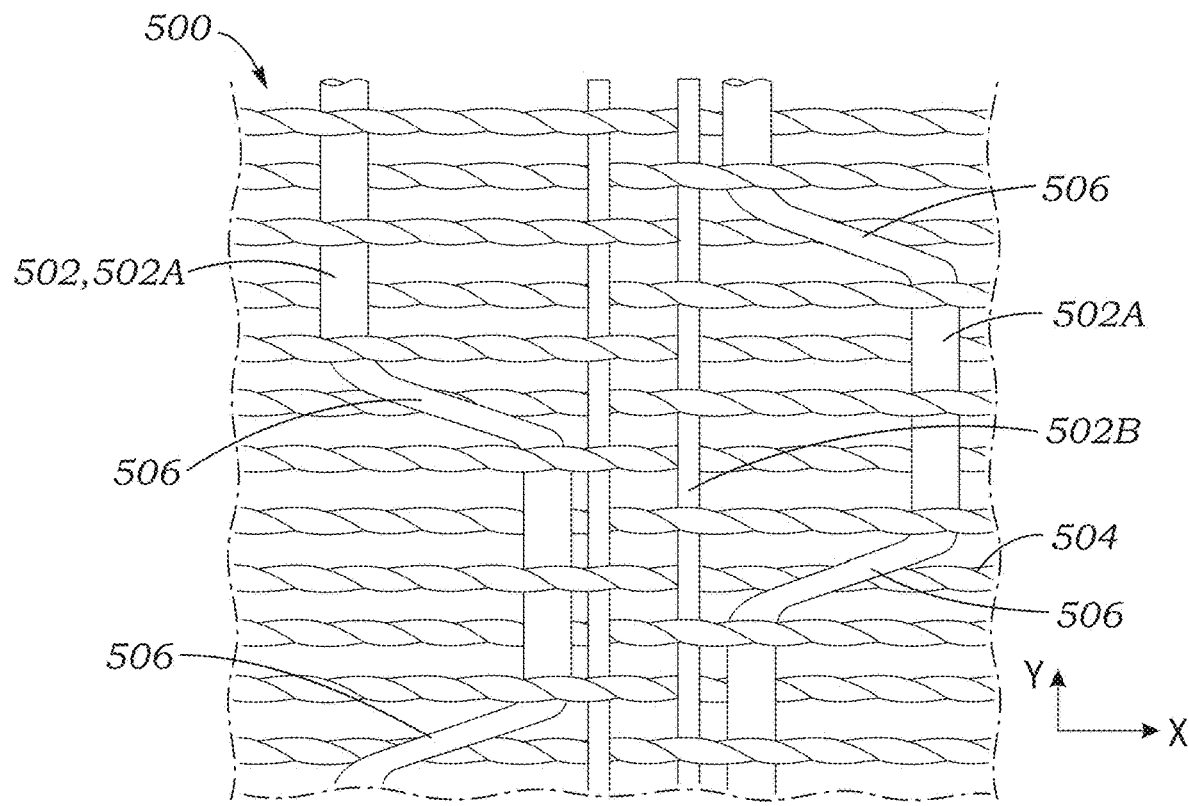
FIGS. 22-25 illustrate various other embodiments of sealing elements with yarns that form loops extending from the sealing elements.

FIGS. 22-25 illustrate additional embodiments of fabric sealing elements that include a plurality of yarns or fibers that extend from the sealing elements to form loops in the manner of a looped pile to increase the surface area available for thrombogenesis and tissue growth. For example, FIG. 22 schematically illustrates a portion of a sealing element 500 including a plurality of first yarns 502 interwoven with a plurality of second yarns 504. In certain embodiments, the first yarns 502 can be warp yarns, and the second yarns 504 can be weft yarns, or vice versa. The warp yarns 502 can be configured to form loops 506 that extend outwardly from the plane of the page, and extend over one or more weft yarns 504. For example, in the embodiment of FIG. 22, the sealing element can comprise warp yarns 502A and warp yarns 502B. The warp yarns 502A can form the loops 506, while one or more warp yarns 502B can be interposed between warp yarns 502A. For example, in the illustrated embodiment, there are two warp yarns 502B between the two warp yarns 502A, although there may be any number of warp yarns 502B depending upon, for example, the desired spacing between the loops 506.

Figure 23:
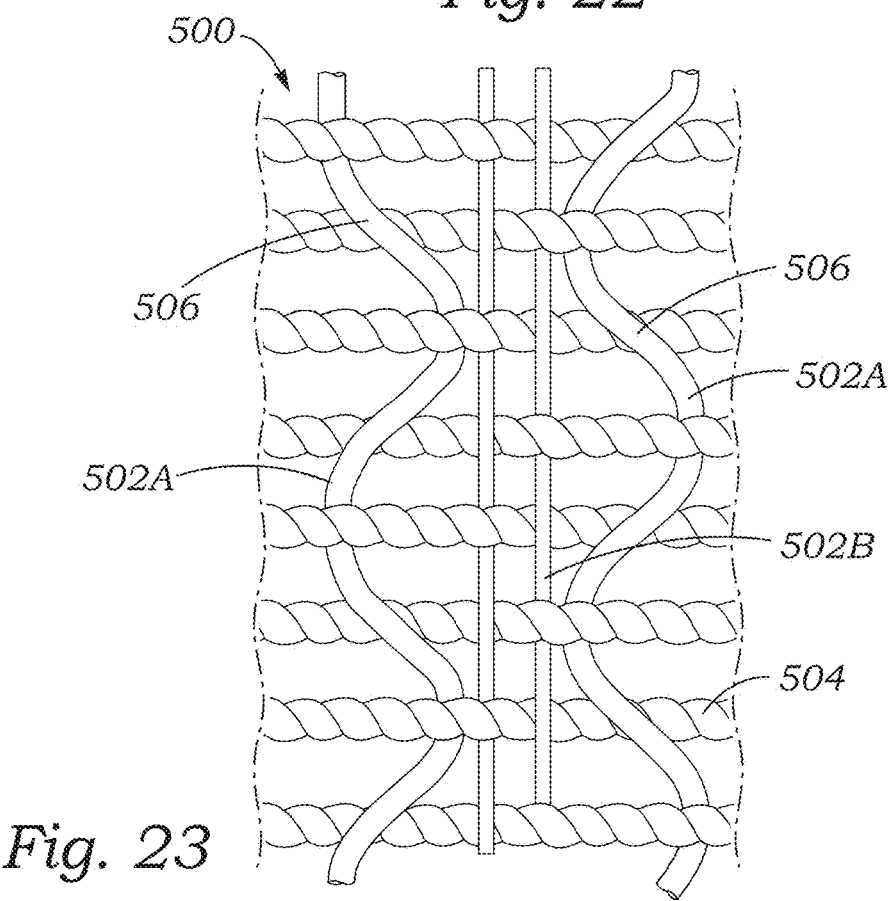
Figure 24:
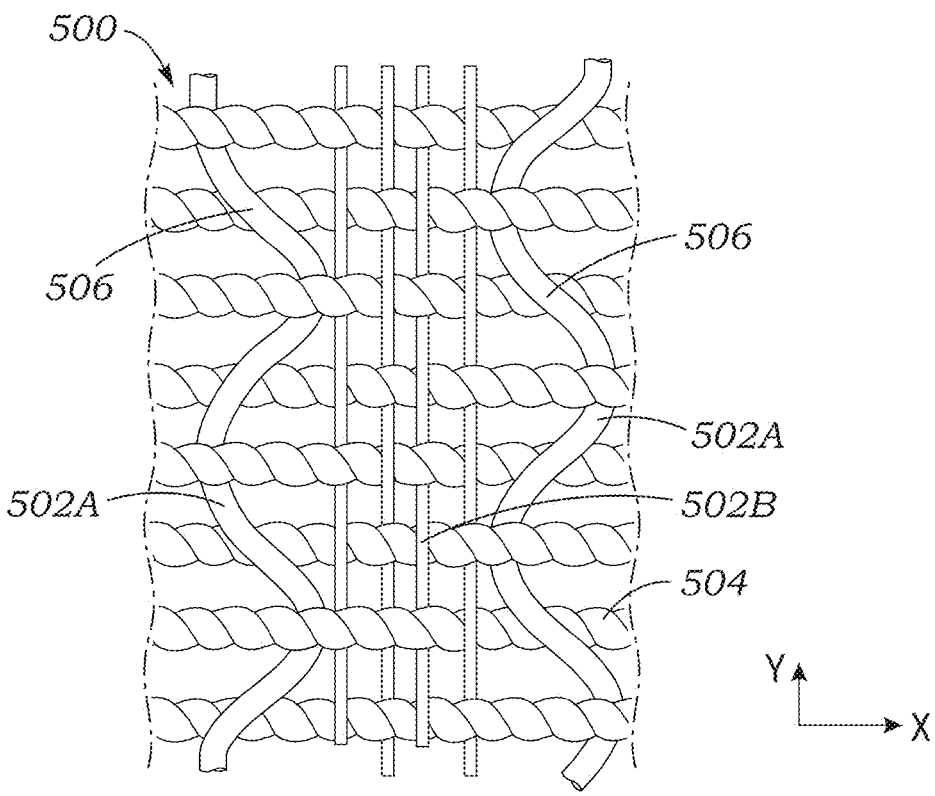
Figure 25:
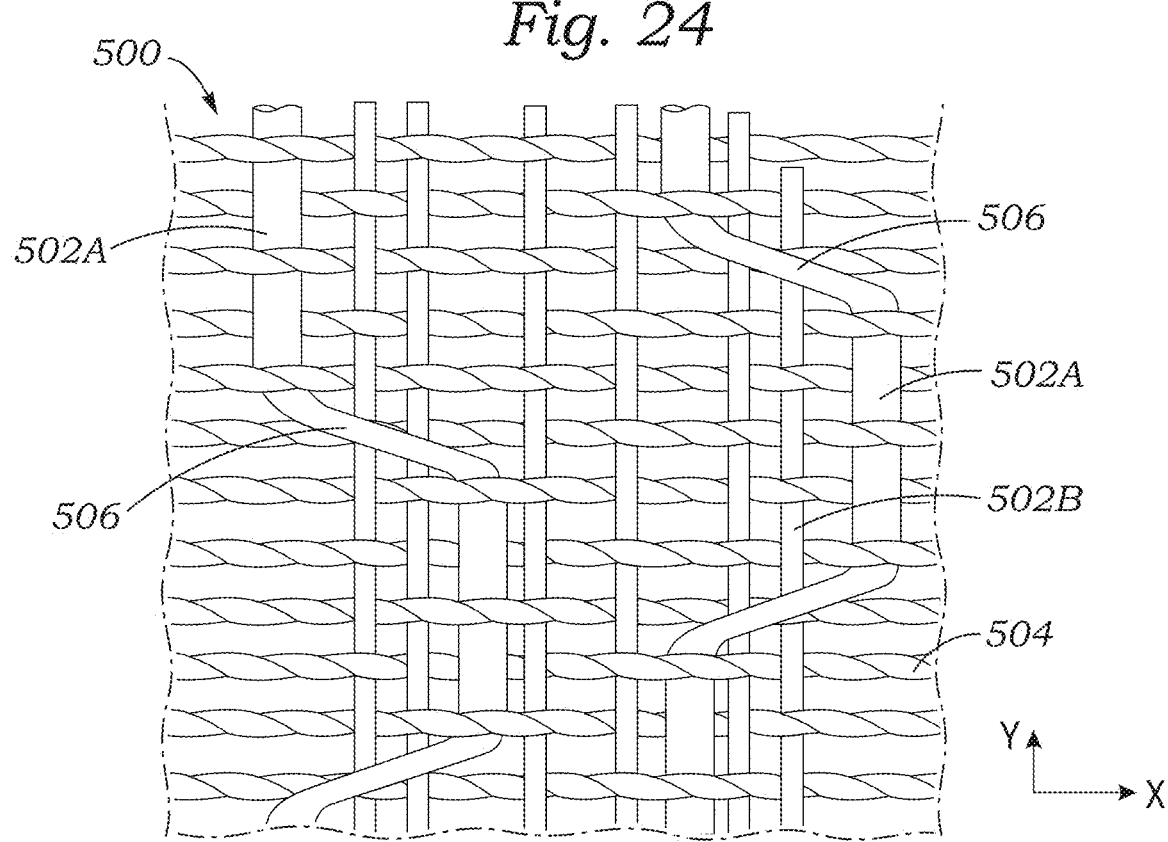

The warp yarns 502A can also change direction where they form the loops 506. For example, in the embodiment of FIG. 22, the loops 506 can extend across one or more weft yarns 504 at an angle to the weft yarns 504. Stated differently, the points where the loops 506 originate and return can be offset from each other along the x-axis (note Cartesian coordinate axes shown). The loops 506 can alternately extend in the positive x-direction and in the negative x-direction such that straight portions of the yarns 502A between loops 506 are offset from each other along the x-axis. This can provide certain advantages, such as preventing movement of or "locking" the warp yarns 502A relative to the weft yarns 504. Additionally, when the sealing member 500 is attached to a prosthetic valve with the warp yarns 502 extending axially in the direction of a longitudinal axis of the valve, the width W of the loops 506 can be oriented perpendicular, or substantially perpendicular, to the direction of blood flow through the valve such that the loops 506 present a relatively large flow obstruction. This can promote blood stasis and sealing around the prosthetic valve. The loop density (e.g., the number of loops per inch) of the pile can be varied by, for example, varying the length of the straight portions of the yarns 502A between the loops 506. Shortening the distance between loops 506 can increase the loop density of the pile, as shown in FIGS. 23 and 24, while increasing the distance between the loops 506 can decrease the loop density of the pile. The width of the loops 506 can be determined by, for example, the number of warp yarns over which the loops extend. For example, in FIG. 25 the loops extend over two warp yarns 502B such that the loops 506 of FIG. 25 are wider relative to the loops 506 of FIG. 22.

In certain embodiments, the loops 506 can be formed using warp-knitting techniques. In certain examples, the first warp yarns 502A can comprise 20 denier, 18 filament (20d/18f) and/or 30d/18f texturized yarns. The second warp yarns 502B can comprise 20d/18f yarns twisted with 12 twists per inch (tpi). In certain examples, the weft yarns 504 can be 20d/18f yarns with 12 tpi. The warp and weft yarns can be made from any of various biocompatible polymers, such as PET, UHMWPE, PTFE, etc. In other embodiments, the warp and/or weft yarns can have any selected denier and/or filament count, and can be made from any suitable natural or synthetic material.

Figure 26:
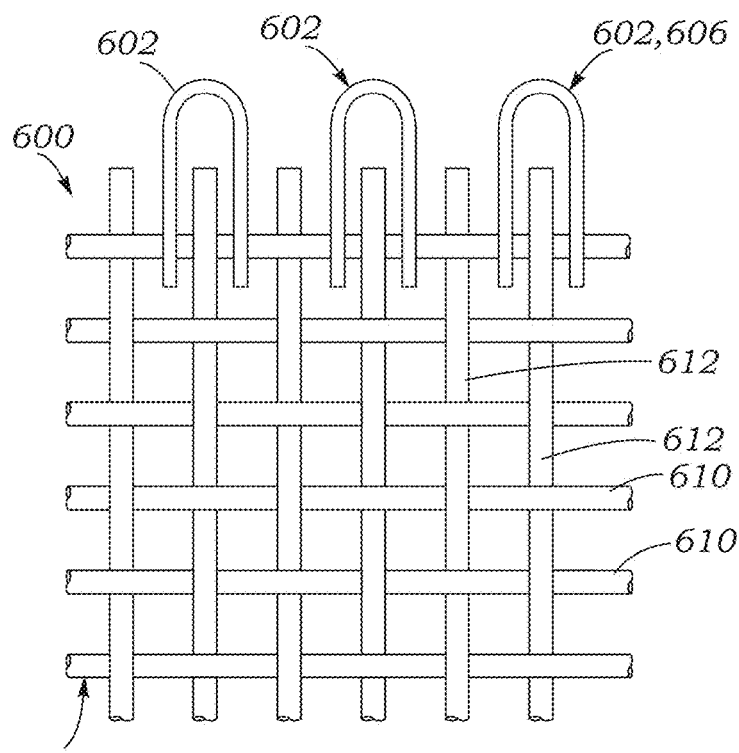
FIG. 26 is a perspective view of a portion of a sealing member including a plurality of loops embroidered into a base skirt fabric, according to one embodiment.
Figure 27:
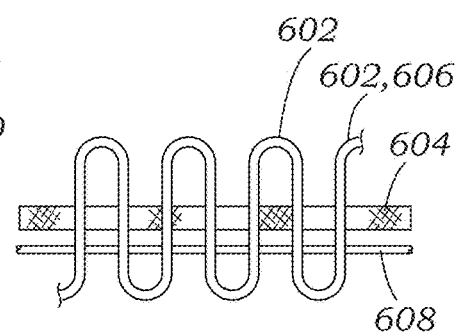
FIG. 27 is a cross-sectional side elevation view of the sealing member of FIG. 26.

In some embodiments, loops may be formed on a prosthetic valve skirt by embroidery. In a representative embroidery technique, a yarn or thread is stitched to or through a base or foundation layer (e.g., a fabric), allowing a variety of shapes or patterns to be produced on the surface of the foundation layer. FIG. 26 illustrates a portion of a skirt 600 including a plurality of loops 602 embroidered into a base skirt fabric 604, according to one embodiment. The base skirt fabric can comprise a plurality of first yarns 610 interwoven with a plurality of second yarns 612 in, for example, a plain weave. Referring to FIG. 27, the loops 602 can be formed using a third yarn configured as an embroidery yarn 606, which may be a relatively high-density yarn or suture. In certain embodiments, in addition to the first or foundation layer 604, the skirt 600 may also optionally include a second layer configured as a locking layer 608. In particular embodiments, the locking layer 608 can comprise a relatively low-density, light, and/or thin yarn or suture that can be used to lock the embroidery yarn 606 on the back of the foundation layer 604.

Figure 28:
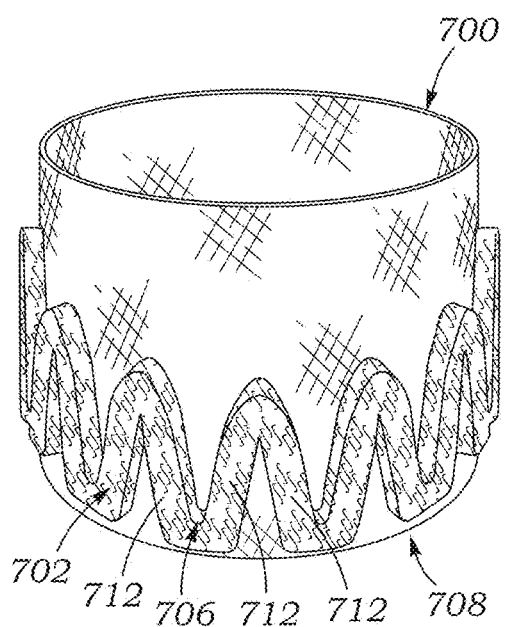
FIGS. 28-30 are perspective views illustrating plush loop portions formed on sealing members in various patterns.
Figure 29:
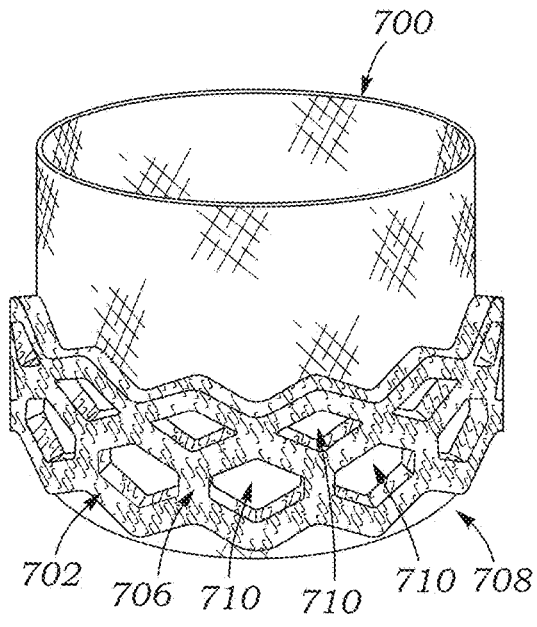
Figure 30:
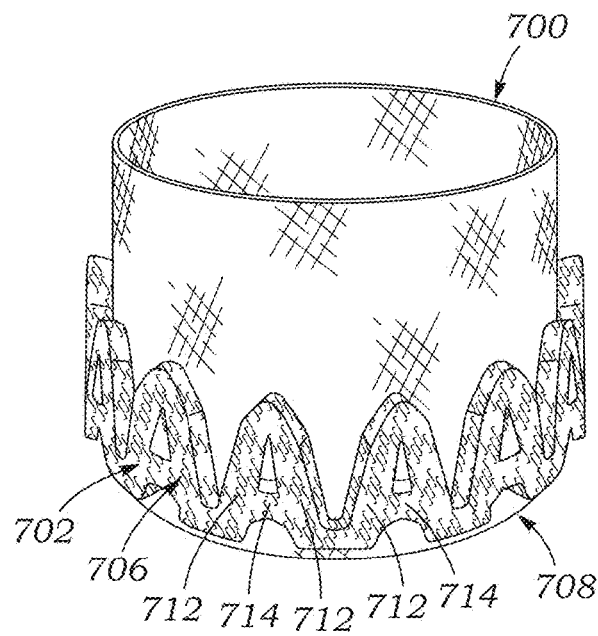

As noted above, loops may be embroidered on the surface of the prosthetic valve skirt having any specified location, length, width, spacing, shape, and/or pattern. FIGS. 28-30 illustrate just a few examples of the patterns that may be produced using the embroidery technique described above. For example, FIG. 28 illustrates a prosthetic valve skirt 700 including a plurality of loops generally indicated at 702 embroidered onto the skirt and forming a plush portion or pile 706. The plush portion 706 can include a plurality of angled portions 712 extending circumferentially around the skirt 700 in a zig-zag pattern from an end portion 708 (e.g., an inflow end portion) of the skirt to midway up the height of the skirt. FIG. 29 illustrates another variation of the plush portion 706 in which the plush portion defines cells 710. In certain embodiments, the cells 710 can correspond to openings or cells defined by the struts of the frame, such as the struts 26 of the prosthetic valve 10 of FIG. 1. In other embodiments, the cells of the plush portion 706 can correspond to the size and shape of the frame openings defined by the struts of the frame 202 of FIG. 9. FIG. 30 illustrates another variation of the plush portion 706 including straight portions 714 extending between adjacent angled portions 712. In certain embodiments, the loops 44 of FIG. 1 can be formed on the underlying fabric of the skirt 30 by embroidery.

Figure 31:
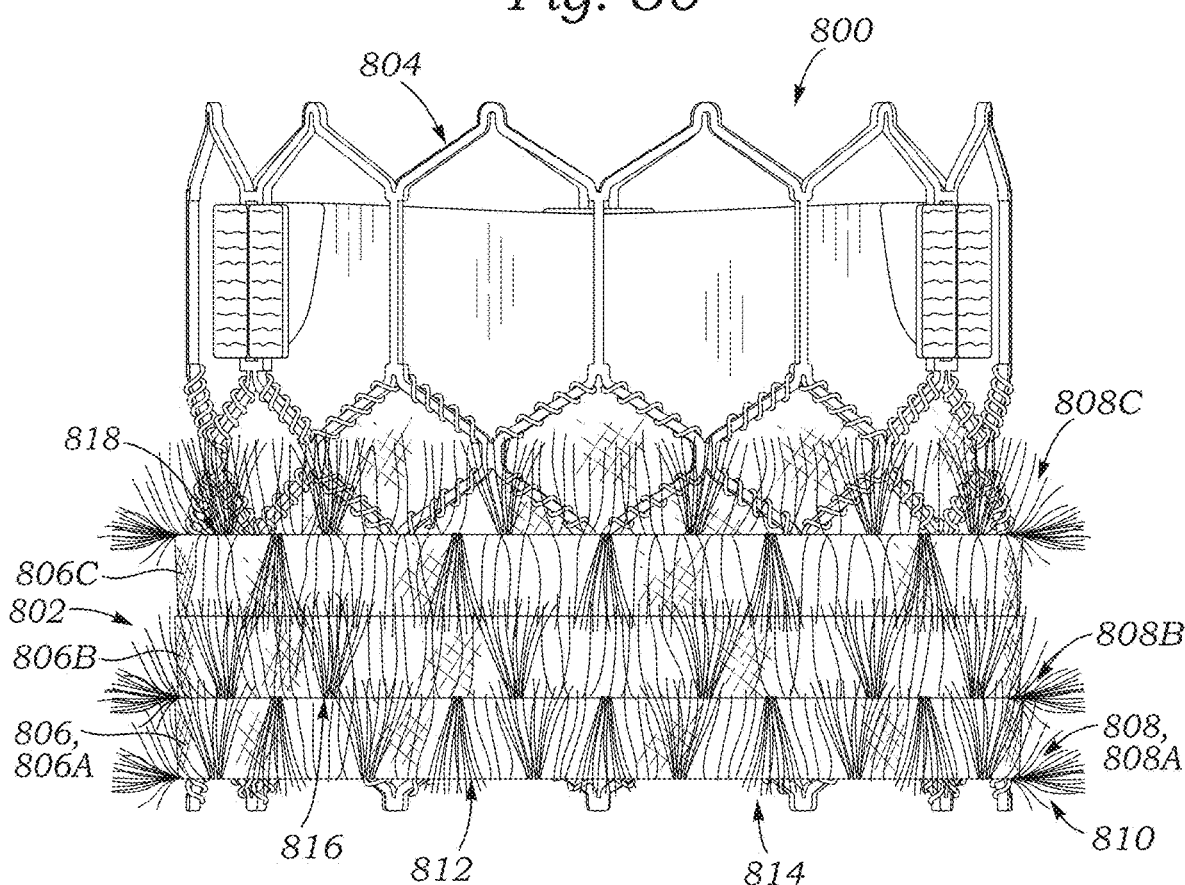
FIG. 31 is a side elevation view of a prosthetic heart valve including a sealing member comprising a plurality of woven fabric strips including fringed portions, according to another embodiment.

FIG. 31 illustrates a prosthetic heart valve 800 including another embodiment of a sealing member or skirt 802 on a frame 804 configured as the frame of the Edwards Lifesciences Corporation SAPIEN® 3 prosthetic heart valve. The skirt 802 can comprise a plurality of woven portions configured as fabric strips 806 extending circumferentially around the frame. Each of the fabric strips 806 can comprise a corresponding fringe portion 808 comprising a plurality of filaments 810 extending radially outwardly at an angle from a circumferential edge portion (e.g., an inflow or outflow edge portion) of the fabric strip 806, similar to the skirt 100 of FIG. 7 above. In the illustrated embodiment, the skirt 802 can comprise three fabric strips 806A-806C having corresponding fringe portions 808A-808C. The fringe portion 808A of the fabric strip 806A can extend from an inflow edge 812 of the fabric strip 806A located proximate an inflow end 814 of the prosthetic valve. The filaments 810 of the fringe portion 808A can extend to about the second row II of strut members (see FIG. 12B). The filaments 810 of the second fabric strip 806B can extend from an inflow edge 816 of the fabric strip 806B, and can extend to about the level of the third row III of struts. The filaments 810 of the third fabric strip 806C can extend from an outflow edge 818 of the fabric strip 806C to about the level of the fourth row IV of struts.

The filaments 810 may comprise or originate from frayed yarns, textured yarns, etc. In certain embodiments, the fabric strips 806 of the sealing member 802 can comprise a yarn density of from 50 to 500 yarns per inch, 100 to 400 yarns per inch, 150 to 350 yarns per inch, or 150 to 300 yarns per inch. In certain embodiments, the fabric strips of the sealing member 802 can have a yarn density of 150 yarns per inch, or 300 yarns per inch. The yarns may have any suitable filament density, such as 5 to 100 filaments per yarn, 10 to 50 filaments per yarn, or 10 to 20 filaments per yarn. In particular embodiments, the yarns can comprise textured yarns having 18 filaments per yarn. The filaments may have thicknesses from 1 μm to 100 μm, 1 μm to 50 μm, or 1 μm to 20 μm. In particular embodiments, the filaments can have a thickness or diameter of 10 μm.

Figure 32:
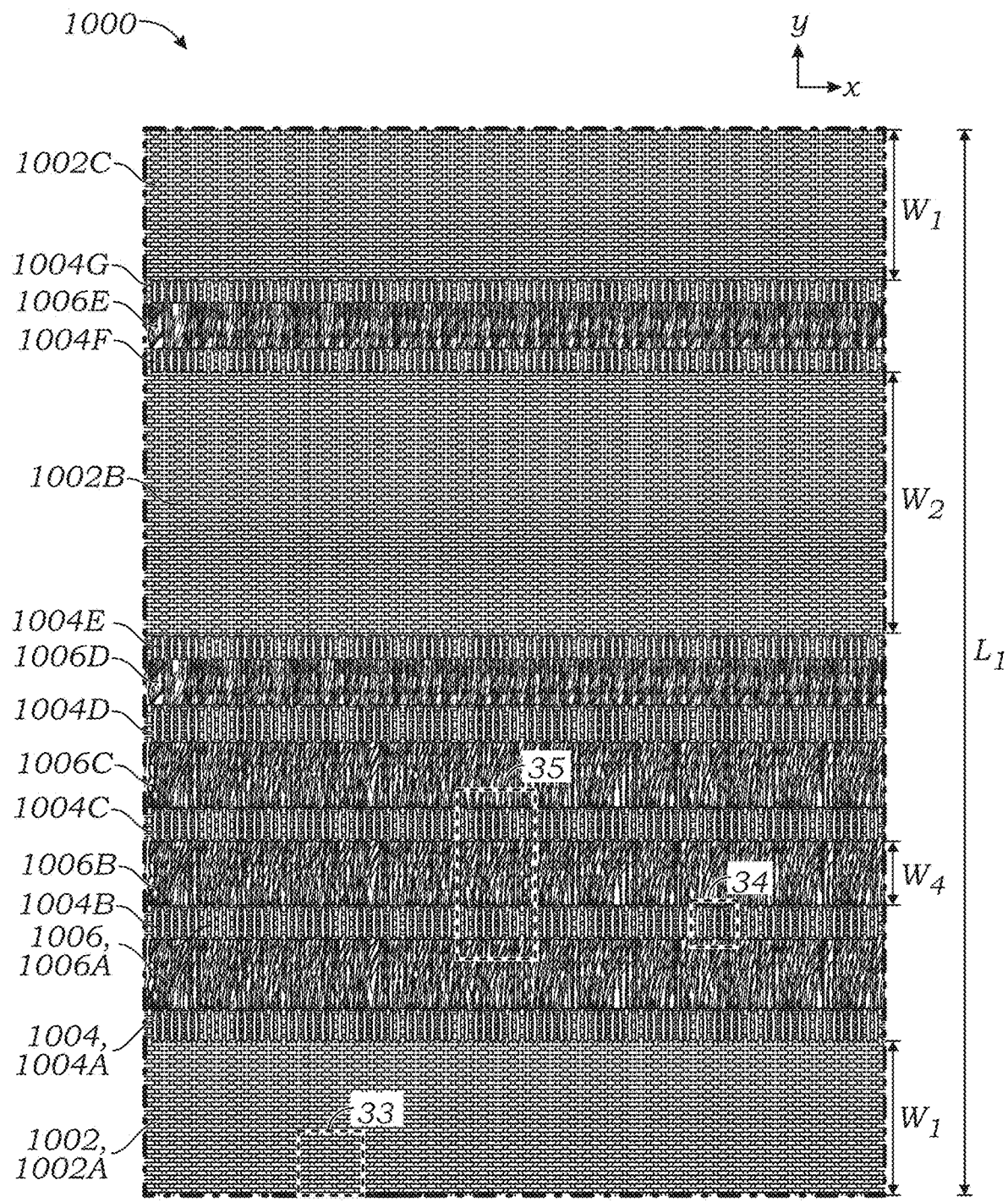
FIG. 32 is a plan view of a sealing member for a prosthetic heart valve including woven portions and floating yarn portions, according to another embodiment.

FIGS. 32-37 show a main cushioning layer, covering, or sealing member 1000, according to another embodiment. The sealing member 1000 can comprise a fabric body having a plurality of woven portions and a plurality of elastic, stretchable portions configured as floating yarn portions, and can be incorporated into any of the prosthetic valve outer coverings described herein. FIG. 32 illustrates the sealing member 1000 in a laid-flat configuration where the x-axis corresponds to the circumferential direction and the y-axis corresponds to the axial direction when the sealing member is attached to a frame of a prosthetic valve. The sealing member 1000 can comprise a plurality of first woven portions 1002 configured as woven strips or stripes extending along the x-axis, a plurality of second woven portions 1004 configured as woven strips or stripes extending along the x-axis, and a plurality of floating yarn portions, strips, or stripes 1006 extending along the x-axis. The various woven and floating yarn portions can be spaced apart from each other along the y-axis. In the illustrated configuration, the first woven portions 1002 can comprise a weave pattern that is different from the weave pattern of the second woven portions 1004, as described in greater detail below.

For example, in the illustrated configuration, the sealing member 1000 can comprise a first woven portion 1002A. Moving in a direction along the positive y-axis, the sealing member 1000 can further comprise a second woven portion 1004A, a floating yarn portion 1006A, a second woven portion 1004B, a floating yarn portion 1006B, a second woven portion 1004C, a floating yarn portion 1006C, a second woven portion 1004D, a floating yarn portion 1006D, a second woven portion 1004E, a first woven portion 1002B, a second woven portion 1004F, a floating yarn portion 1006E, a second woven portion 1004G, and a first woven portion 1002C at the opposite end of the sealing member from the first woven portion 1002A. In other words, the first woven portion 1002B and each of the floating yarn portions 1006A-1006E can be located between two second woven portions 1004 such that the first woven portion 1002B and each of the floating yarn portions 1006A-1006E are bounded or edged in a direction along the x-axis by respective second woven portions 1004.

Figure 33:
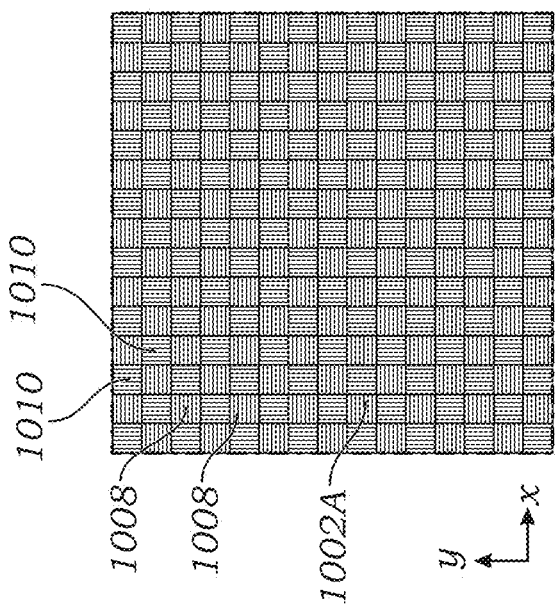
FIG. 33 is a magnified view of a first woven portion of the sealing member of FIG. 32.

Referring to FIGS. 32 and 33, the sealing member 1000 can comprise a plurality of first yarns 1008 oriented generally along the x-axis and a plurality of second yarns 1010 oriented generally along the y-axis. In certain configurations, the first yarns 1008 can be warp yarns, meaning that during the weaving process the yarns 1008 are held by the loom, while the second yarns 1010 are weft yarns, which are interwoven with the warp yarns by a moving shuttle or weft-carrying mechanism during the weaving process. However, in other embodiments the first yarns 1008 may be weft yarns and the second yarns 1010 may be warp yarns.

Each of the first yarns 1008 and the second yarns 1010 can comprise a plurality of constituent filaments 1012 that are spun, wound, twisted, intermingled, interlaced, etc., together to form the respective yarns. Exemplary individual filaments 1012 of the second yarns 1010 can be seen in FIGS. 33-36. In some embodiments, the first yarns 1008 can have a denier of from about 1 D to about 200 D, about 10 D to about 100 D, about 10 D to about 80 D, about 10 D to about 60 D, or about 10 D to about 50 D. In some embodiments, the first yarns 1008 can have a filament count of 1 to about 600 filaments per yarn, about 10 to about 300 filaments per yarn, about 10 to about 100 filaments per yarn, about 10 to about 60 filaments per yarn, about 10 to about 50 filaments per yarn, or about 10 to about 30 filaments per yarn. In particular embodiments, the first yarns 1008 can have a denier of about 40 D and a filament count of 24 filaments per yarn. The first yarns 1008 may also be twisted yarns or non-twisted yarns. In the illustrated embodiment, the filaments 1012 of the first yarns 1008 are not texturized. However, in other embodiments, the first yarns 1008 may comprise texturized filaments.

The second yarns 1010 can be texturized yarns comprising a plurality of texturized filaments 1012. For example, the filaments 1012 of the second yarns 1010 can be texturized, for example, by twisting the filaments, heat-setting them, and untwisting the filaments as described above. In some embodiments, the second yarns 1010 can have a denier of from about 1 D to about 200 D, about 10 D to about 100 D, about 10 D to about 80 D, or about 10 D to about 70 D. In some embodiments, a filament count of the second yarns 1010 can be from 1 filament per yarn to about 100 filaments per yarn, about 10 to about 80 filaments per yarn, about 10 to about 60 filaments per yarn, or about 10 to about 50 filaments per yarn. In particular embodiments, the second yarns 1010 can have a denier of about 68 D and a filament count of about 36 filaments per yarn.

The first yarns 1008 and the second yarns 1010 can be woven together to form the woven portions of the sealing member, as noted above. For example, in the first woven portions 1002A-1002C, the first and second yarns 1008, 1010 can be woven together in a plain weave pattern in which the second yarns 1010 (e.g., the weft yarns) pass over a first yarn 1008 (e.g., a warp yarn) and then under the next first yarn in a repeating pattern. This weave pattern is illustrated in detail in FIG. 33. In some embodiments, the density of the first yarns 1008 can be from about 10 yarns per inch to about 200 yarns per inch, about 50 yarns per inch to about 200 yarns per inch, or about 100 yarns per inch to about 200 yarns per inch. In certain embodiments, the first woven portion 1002A and the first woven portion 1002C can be configured as selvedge portions, and can have a lower yarn density than the first woven portion 1002B to facilitate assembly on a valve frame. Other weave patterns may also be used, such as over two under two, over two under one, etc. The first woven portions may also be woven in plain weave derivative patterns such as twill, satin, or combinations of any of these.

Figure 34:
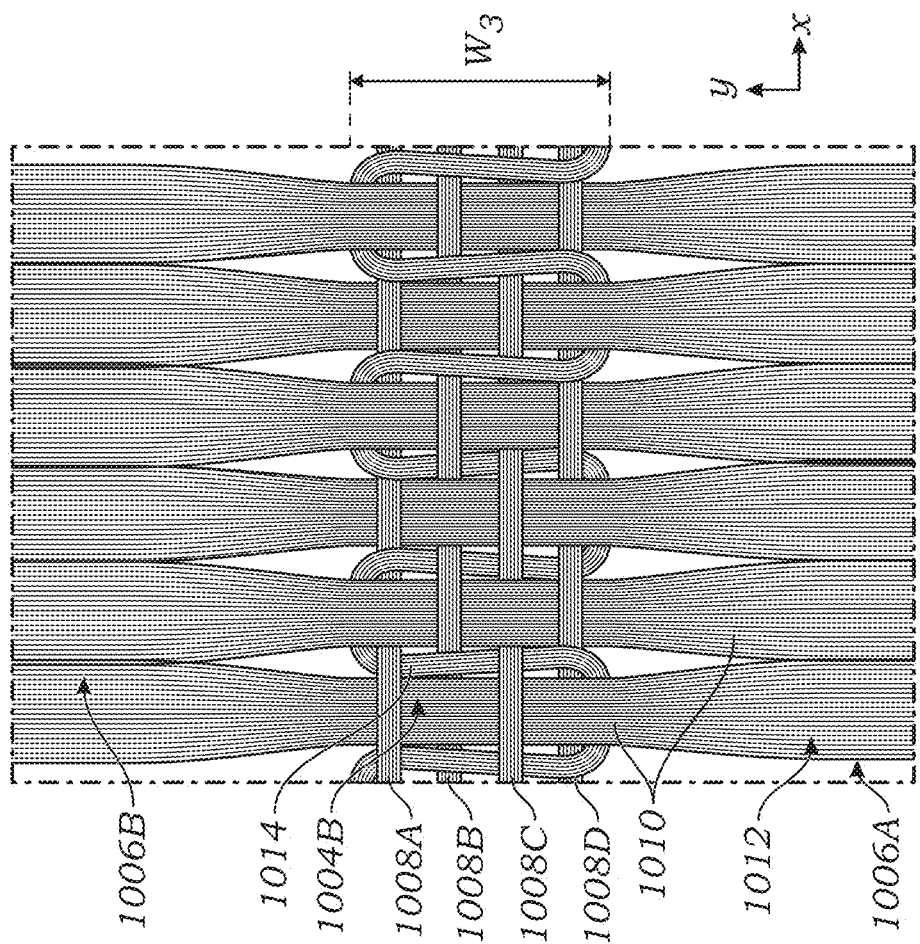
FIG. 34 is a magnified view of a second woven portion of the sealing member of FIG. 32.

In the second woven portions 1004A-1004G, the first and second yarns 1008, 1010 can be interwoven in another pattern that is different from the weave pattern of the first woven portions 1002A-1002C. For example, in the illustrated embodiment, the first and second yarns 1008, 1010 can be woven together in a leno weave pattern in the second woven portions 1004A-1004G. FIG. 34 illustrates the leno weave of the second woven portion 1004B in greater detail. With reference to FIG. 34, the leno weave can comprise one or more leno yarns or "leno ends" 1014, and four first yarns 1008A, 1008B, 1008C, and 1008D, also referred to as "warp ends." The pattern illustrated in FIG. 34 includes a single leno yarn 1014 in the manner of a half-leno weave. However, in other embodiments, the leno weave pattern may be a full-leno weave comprising two intertwining leno yarns 1014, or other leno-derived weaves. Examples of various leno weaves and associated weaving techniques are illustrated in FIGS. 39A-39J.

In the half-leno weave illustrated in FIG. 34, the first yarns 1008A-1008D can extend parallel to the x-axis, and the second yarns 1010 can be interwoven with the first yarns 1008A-1008D in, for example, a plain weave. The leno yarn 1014 can weave around the first yarns 1008A-1008D such that the leno yarn 1014 crosses over, or on top of, the first yarns 1008A-1008D with each pass in the positive y-direction, crosses beneath or behind the next second yarn 1010 in the x-direction, and extends back over the first yarns 1008A-1008D in the negative y-direction. This pattern can be repeated along the length of the second woven portion 1004B. In this manner, the second woven portions 1004 can be relatively narrow, strong woven portions spaced axially from each other along the frame when the sealing element is mounted to a frame. The leno yarn 1014 can serve to keep the first yarns 1008A-1008D and the second yarns 1010 in place with respect to each other as the prosthetic valve is crimped and expanded, and can impart strength to the second woven portions 1004 while minimizing width.

In certain embodiments, each of the second woven portions 1004A-1004G can comprise the leno weave pattern described above. In other embodiments, one or more of the second woven portions 1004A-1004G may be configured differently, such as by incorporating more or fewer first yarns 1008 in the leno weave, having multiple leno ends woven around multiple groupings of yarns 1008, etc. In yet other embodiments, a chemical locking method can be used where the leno weave and/or a plain weave includes warp yarns having core-sheath construction filaments. The sheath of the individual filaments can be made of low-melt temperature polymers such as biocompatible polypropylene, and the core of the filaments be made of another biocompatible polymer such as polyester. After the weaving process, the heat setting process described below can enable the softening and/or melting of the sheath. Upon cooling, the softened sheath polymer can bond the core polyester filaments together. This can create a bonded body enabling locking of the woven structure.

Referring again to FIG. 32, the floating yarn portions 1006 can comprise yarns extending in only one axis between respective second woven portions 1004 that are spaced apart from each other along the y-axis. For example, taking the floating yarn portion 1006A as a representative example, the floating yarn portion 1006A can comprise a plurality of second yarns 1010 that exit the leno weave of the second woven portion 1004A, extend across the floating yarn portion 1006A, and are incorporated into the leno weave of the second woven portion 1004B. In some embodiments, the density of the second yarns in the floating yarn portions 1006 can be from about 10 to about 200 yarns per inch, about 50 to about 200 yarns per inch, or about 100 to about 200 yarns per inch. In particular embodiments, the density of the second yarns 1010 can be about 60-80 yarns per inch. In other embodiments, the floating yarn portions can include first yarns 1008 disposed under or over, but not interwoven with, the second yarns 1010 such that the second yarns float over the first yarns or vice versa. In yet other embodiments, the floating yarn portions may instead be configured as any other elastically stretchable structure, such as elastically stretchable woven, knitted, braided, or non-woven fabrics, or polymeric membranes, to name a few, that is elastically stretchable at least in the axial direction of the prosthetic valve.

In the illustrated embodiment, each of the woven portions 1002A-1002C and 1004A-1004G, and each of the floating yarn portions 1006A-1006E can have width dimensions in the y-axis direction. The widths of the constituent portions can be configured such that the overall length $L_1$ (FIG. 32) of the sealing member 1000 generally corresponds to the axial length of a prosthetic heart valve in the expanded configuration. For example, in the illustrated embodiment the first woven portions 1002A and 1002C can each have a width $W_1$. In certain embodiments, the width $W_1$ can be configured such that portions of the first woven portions 1002A and 1002C can be folded over the inflow and outflow ends of the frame of a prosthetic valve.

The first woven portion 1002B can have a width $W_2$. With reference to FIG. 12B, when the sealing member 1000 is used in combination with the frame of the Edwards Lifesciences SAPIEN® 3 prosthetic heart valve, the width $W_2$ can be configured to correspond to the axial dimension of the frame openings defined by the strut members between the fourth row IV and the fifth row V of struts. In some embodiments, the width $W_2$ of the first woven portion 1002B can be about 2 mm to about 20 mm, about 2 mm to about 12 mm, or about 3 mm to about 10. In particular embodiments, the width $W_2$ can be about 7 mm.

The second woven portions 1004A-1004G can have widths $W_3$ (FIG. 34). In the illustrated embodiment, all of the second woven portions 1004A-1004G have the width $W_3$, but one or more of the second woven portions may also have different widths. In certain embodiments, the width $W_3$ can be relatively short, such as about 0.1 mm to about 3 mm, about 0.1 mm to about 2 mm, or about 0.1 mm to about 1 mm. In particular embodiments, the width $W_3$ can be about 1 mm.

With reference to FIGS. 32 and 35-38, in certain embodiments the sealing member 1000, and in particular the floating yarn portions 1006A-1006E, can be resiliently stretchable between a first, natural, or relaxed configuration (FIG. 32 and FIG. 35) corresponding to the radially expanded state of the prosthetic valve, and a second, elongated, or tensioned configuration (FIGS. 37 and 38) corresponding to the radially compressed state of the prosthetic valve. Thus, the floating yarn portions 1006A-1006E can have initial widths $W_4$ when the sealing member 1000 is in the relaxed, unstretched state. FIG. 35 illustrates a portion of the floating yarn portion 1006B in the natural, relaxed state. When the fabric is in the relaxed state, the textured filaments 1012 of the second yarns 1010 can be kinked and twisted in many directions such that the floating yarn portion 1006B has a bulky, billowy, or pillow-like quality. When tensioned, the kinks, twists, etc., of the filaments 1012 can be pulled at least partially straight along the y-axis, causing the second yarns 1010 to elongate. With reference to FIG. 36, the width of the floating yarn portions 1006 can thus increase to a second width $W_5$ that is larger than the initial width $W_4$.

Figure 37:
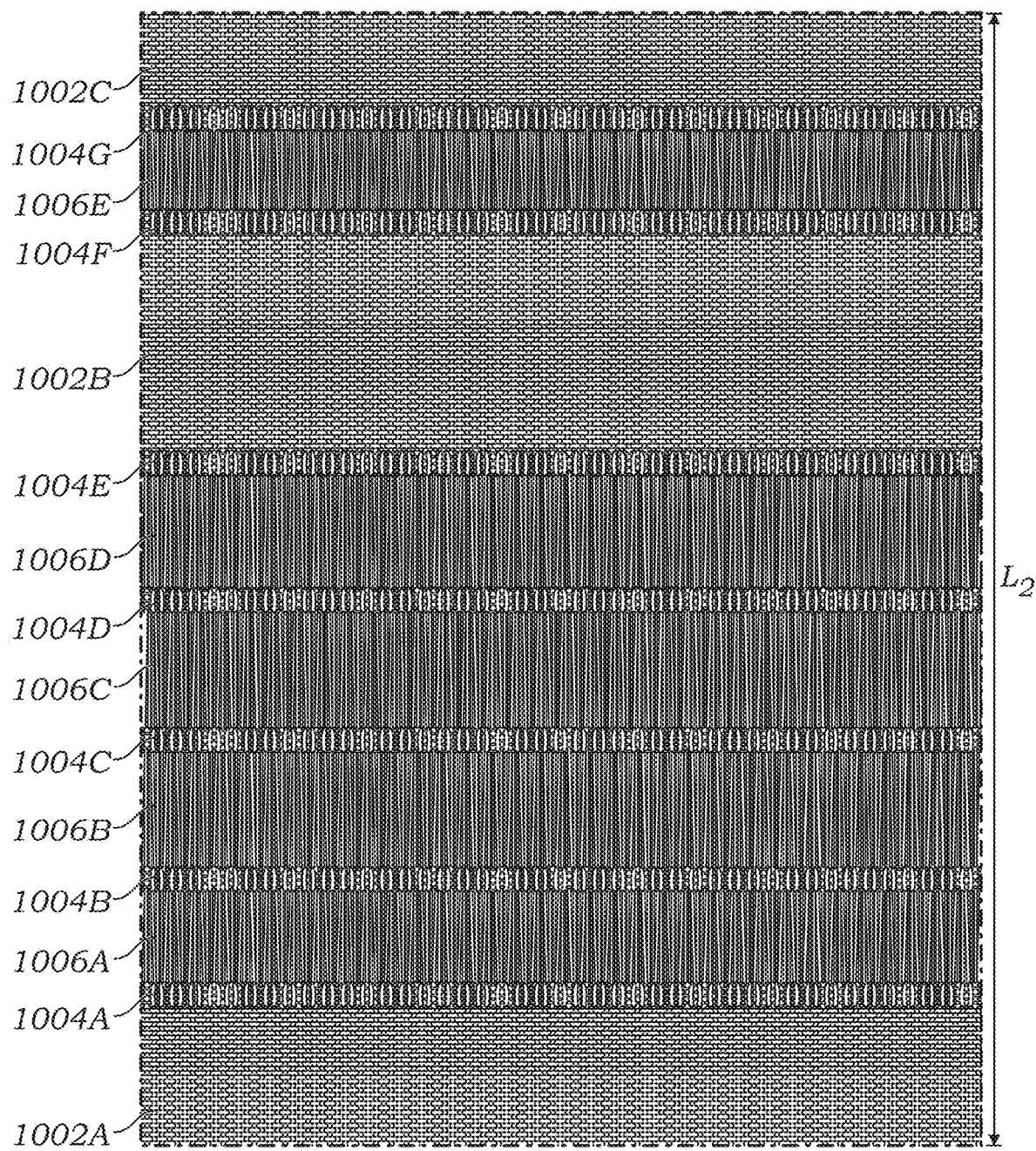
FIG. 37 is a plan view of the sealing member of FIG. 32 in a stretched state.

The cumulative effect of the floating yarn portions 1006A-1006E increasing in width from the initial width $W_4$ to the second width $W_5$ is that the overall axial dimension of the sealing member 1000 can increase from the initial length $L_1$ (FIG. 32) to a second overall length $L_2$ (FIG. 37) that is greater than the first length $L_1$. FIG. 37 illustrates the sealing member 1000 in the stretched configuration with the second yarns 1010 of the floating yarn portions 1006A-1006E straightened under tension such that the overall length of the sealing member increases to the second length $L_2$. In certain embodiments, the size, number, spacing, etc., of the floating yarn portions 1006, and the degree of texturing of the constituent second yarns 1010, can be selected such that the second length $L_2$ of the sealing member 1000 corresponds to the length of a frame of a prosthetic valve when the prosthetic valve is crimped for delivery on a delivery apparatus. In particular embodiments, the relaxed initial width $W_4$ of the floating yarn portions 1006 can be about 1 mm to about 10 mm, about 1 mm to about 8 mm, or about 1 mm to about 5 mm. In particular embodiments, the initial width $W_4$ can be about 4 mm.

Figure 38:
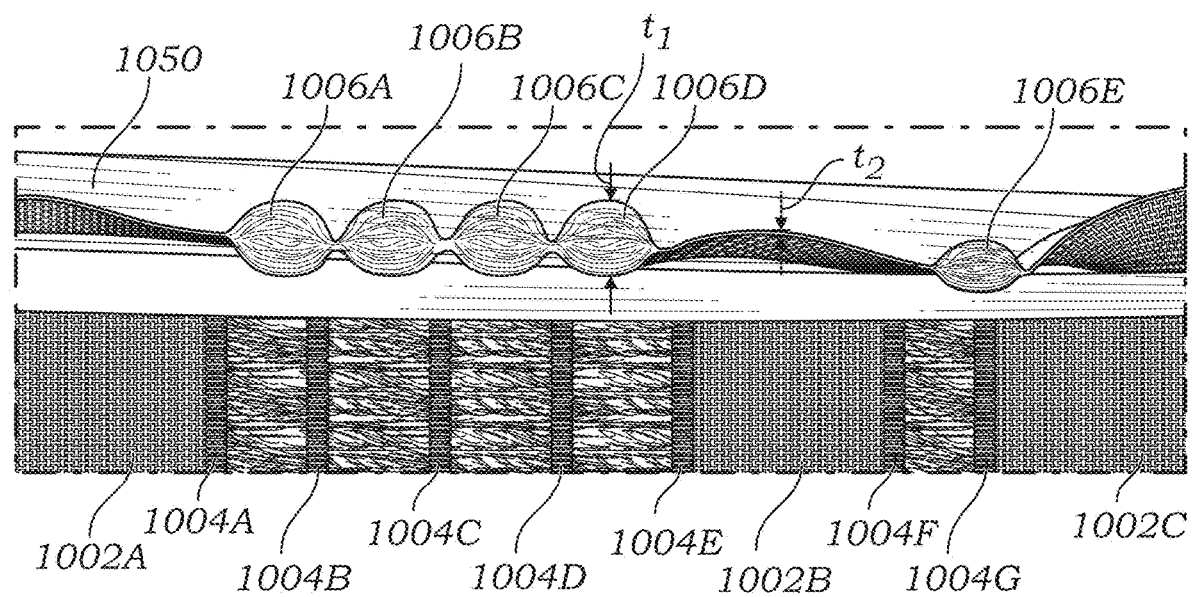
FIG. 38 is a perspective view illustrating an edge portion of the sealing member of FIG. 32.

FIG. 38 illustrates an edge portion of the sealing member 1000 gripped between a pair of grippers 1050. In certain embodiments the bulky, billowy nature of the texturized yarns 1010 in the floating yarn portions 1006 can result in the floating yarn portions 1006 having a thickness $t_1$ that is greater than a thickness $t_2$ of the woven portions 1002 and 1004. For example, in certain embodiments the thickness $t_1$ of the floating yarn portions 1006 can be two times, three times, four times, five times, six times, or even ten times greater than the thickness $t_2$ of the woven portions 1002 and 1004, or more, when the sealing member is in the relaxed state. This can allow the floating yarn portions 1006 to cushion the native leaflets between the valve body and/or against an anchor or ring into which the prosthetic valve is implanted. The floating yarn portions 1006 can also occupy voids or space in the anatomy, and/or promote tissue growth into the floating yarn portions, as in the embodiments described above. When tension is applied to stretch the floating yarn portions 1006, the thickness $t_1$ can decrease as the texturized second yarns 1010 straighten. In certain embodiments, the thickness $t_1$ can be equal or nearly equal to the thickness $t_2$ of the woven portions 1002 and 1004 when the sealing member is in the tensioned state. When the tension on the sealing member 1000 is released, such as during expansion of the prosthetic valve, the yarns 1012 can resume their texturized shape and the thickness of the floating yarn portions 1006 can return to the initial thickness $t_1$.

In certain embodiments, the floating yarn portions 1006A-1006E can be configured such that the sealing member 1000 can elongate by about 10% to about 500%, about 10% to about 300%, about 10% to about 200%, about 10% to about 100%, about 10% to about 80%, or about 10% to about 50%. In particular embodiments, the floating yarn portions 1006A-1006E can be configured to allow the sealing member 1000 to elongate by about 30%, corresponding to the elongation of the frame 1022 between the expanded and crimped configurations. As noted above, the increase in width of the floating yarn portions 1006A-1006E can also result in a corresponding decrease in thickness of the floating yarn portions, reducing the crimp profile of the prosthetic valve during delivery.

In some embodiments, the first and second yarns 1008 and 1010 can comprise any of various biocompatible thermoplastic polymers such as PET, Nylon, ePTFE, UHMWPE, etc., or other suitable natural or synthetic fibers. In certain embodiments, the sealing member 1000 can be woven on a loom, and can then be heat-treated or heat-set to achieve the desired size and configuration. For example, depending upon the material selected, heat-setting can cause the sealing member 1000 to shrink. Heat-setting can also cause a texturizing effect, or increase the amount of texturizing, of the second yarns 1010. After heat treatment, the openings 1016 can be created in the first woven portion 1002B (e.g., by laser cutting), and the sealing member can be incorporated into an outer covering such as the covering 1018 for assembly onto a prosthetic valve. In some embodiments, the openings 1016 can also be created before heat treatment.

The loops, filaments, floating portions, etc., of the prosthetic sealing members described herein can be configured to promote a biological response in order to form a seal between the prosthetic valve and the surrounding anatomy, as described above. In certain configurations, the sealing elements described herein can be configured to form a seal over a selected period of time. For example, in certain embodiments, the open, porous nature of the loops, filaments, yarns, etc., can allow a selected amount of paravalvular leakage around the prosthetic valve in the time period following implantation. The amount paravalvular leakage past the seal structure may be gradually reduced over a selected period of time as the biological response to the loops, filaments, yarns, etc., causes blood clotting, thrombus formation, etc. In some embodiments, the sealing members, and in particular the loops, filaments, yarns, etc., of the paravalvular sealing structure, may be treated with one or more agents that inhibit the biological response to the sealing structures. For example, in certain embodiments, the loops, filaments, yarns, etc., may be treated with heparin. In certain embodiments, the amount or concentration of the agent(s) may be selected such that the agents are depleted after a selected period of time (e.g., days, weeks, or months) after valve implantation. As the agent(s) are depleted, the biological response to the loops, filaments, yarns, etc., of the sealing structures may increase such that a paravalvular seal forms gradually over a selected period of time. This may be advantageous in patients suffering from left atrial remodeling (e.g., due to mitral regurgitation), by providing an opportunity for the remodeling to reverse as regurgitation past the prosthetic valve is gradually reduced.

Figure 39A:
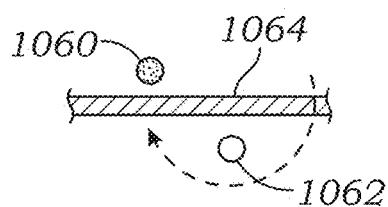
FIGS. 39A-39J illustrate various examples of leno weave patterns and leno weaving techniques.
Figure 39B:
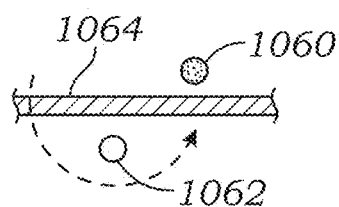

FIGS. 39A-39J illustrate various leno weaves and leno weaving techniques that may be used to produce the sealing member 1000, or any of the other sealing members described herein. FIG. 39A is a cross-sectional view illustrating a shed (e.g., the temporary separation of warp yarns to form upper and lower warp yarns) in which a leno yarn, "leno end," or "crossing end" 1060 forms the top shed on the left of the figure above a weft yarn 1064 and a standard warp yarn 1062 forms the bottom shed. FIG. 39B illustrates a successive shed in which the leno yarn 1060 forms the top shed on the right of the standard warp yarn 1062. In FIGS. 39A and 39B, the leno yarn 1060 may cross under the standard yarn 1062 in a pattern known as bottom douping. Alternatively, the leno yarn 1060 may cross over the standard yarn 1062, known as top douping, as in FIGS. 39H and 39I.

Figure 39C:
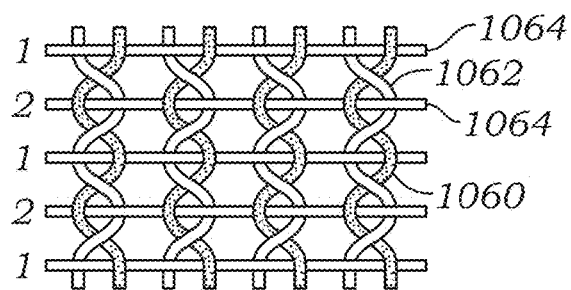
Figure 39D:
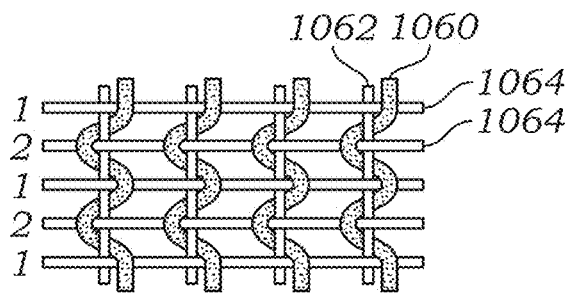

FIG. 39C illustrates a leno weave interlacing pattern produced when one warp beam is used on a loom, and the distortion or tension of the leno yarns 1060 and the standard yarns 1062 is equal such that both the yarns 1060 and the yarns 1062 curve around the weft yarns 1064. FIG. 39D illustrates a leno weave lacing pattern produced when multiple warp beams are used, and the leno yarns 1060 are less tensioned than the standard yarns 1062 such that the standard yarns 1062 remain relatively straight in the weave, and perpendicular to the weft yarns 1064, while the leno yarns 1060 curve around the standard yarns 1062.

Figure 39E:
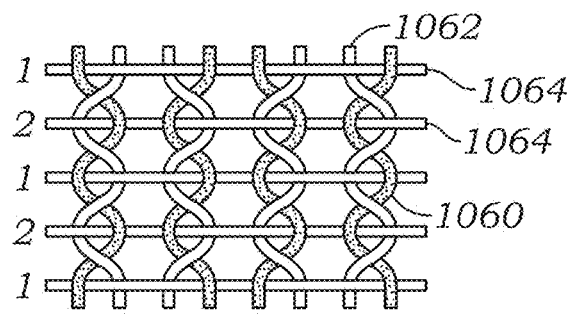
Figure 39F:
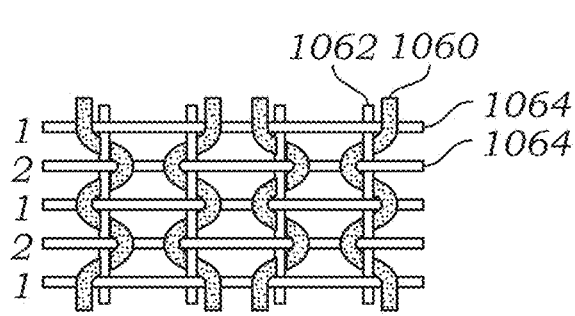

FIG. 39E illustrates an interlacing pattern corresponding to FIG. 39C, but in which alternate leno yarns 1060 are point-drafted (e.g., a technique in which the leno yarns are drawn through heddles) such that adjacent leno yarns 1060 have opposite lacing directions. FIG. 39F illustrates an interlacing pattern corresponding to FIG. 39D, but in which the leno yarns 1060 are point-drafted such that adjacent leno yarns have opposite lacing directions.

Figure 39G:
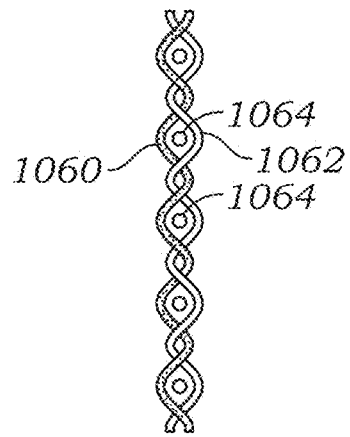
Figure 39H:
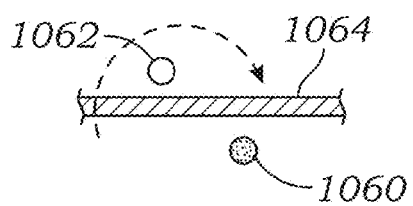
Figure 39I:
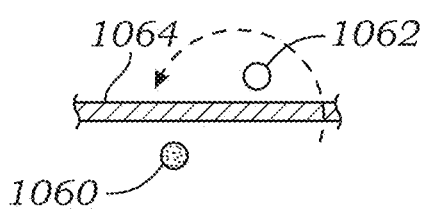

FIG. 39G is a cross-sectional view of a plain leno weave structure taken through the weft yarns 1064.

Figure 39J:
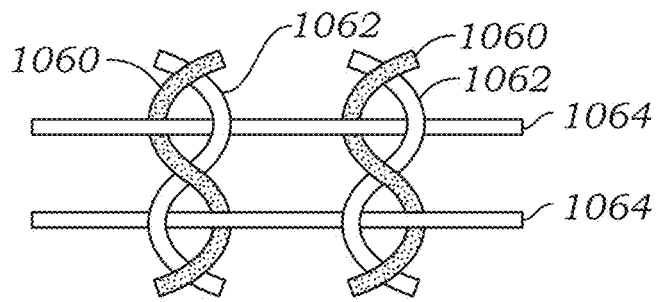

FIG. 39J illustrates a representative leno weave as viewed from the reverse side of the fabric.

Example 1

In a first representative example, an acute animal trial was conducted in which prosthetic heart valves including various skirts of the type shown in FIG. 31 were implanted in the aortic valves of sheep. A first prosthetic valve that was tested included a sealing member or skirt with a yarn density of 300 yarns per inch, in which the yarns had a fringe or filament density of 18 filaments per yarn. A second prosthetic valve had a skirt with a yarn density of 150 yarns per inch, in which the yarns had a filament density of 18 filaments per yarn. A prosthetic valve having no exterior skirt was also implanted as a control.

Prior to implantation, the prosthetic valves were partially crimped, and a stack of annuloplasty rings (e.g., two concentrically stacked annuloplasty rings) were attached around the exterior of the prosthetic valves by suturing. Each stack of annuloplasty rings had a plastic cable tie cinched around the bodies of the annuloplasty rings. The stacks of annuloplasty rings were attached to the prosthetic valves such that the heads of the cable ties were located between the outer skirt of the prosthetic valve and the bodies of the annuloplasty rings. In other words, the heads of the cable ties served to space the bodies of the annuloplasty rings away from the prosthetic valves such that an axially-extending channel was defined between the outer skirt and the annuloplasty rings on both sides of the cable tie head in order to induce paravalvular leakage past the prosthetic valves. For the control prosthetic valve without an exterior skirt, the head of the cable tie spaced the annuloplasty rings away from the exterior surface of the prosthetic valve frame.

The prosthetic valves were implanted in a surgical procedure. A baseline amount of paravalvular leakage through the space between the prosthetic valve frame and the stack of annuloplasty rings was determined using echocardiography and/or angiography while the patient was heparinized. Heparinization was then reversed (e.g., by administration of protamine sulfate), and paravalvular leakage was then assessed using echocardiography and angiography over a period of 5 to 30 minutes. The prosthetic valves were then surgically retrieved.

For the first prosthetic valve having the skirt with the yarn density of 300 yarns per inch, no paravalvular leakage was observed before or after heparin reversal. Upon explant, the space between the outer skirt and the attached annuloplasty rings had become completely sealed by thrombus formation, and the head of the cable tie had become at least partially encapsulated by one or more thrombi.

For the second prosthetic valve having the skirt with the yarn density of 150 yarns per inch, paravalvular leakage having an angiographic grade of 2+ was observed by echocardiography, and a grade of 1+ by angiography, before heparin reversal. As used herein, reference to "paravalvular leakage" or "regurgitation" graded at, e.g., 1+, 2+, 3+, or 4+ refers to the angiographic grading guidelines provided by the American Society of Echocardiography using assessment techniques including, for example, echocardiography, angiography, color flow Doppler, fluoroscopy, etc. (Zoghbi et al., ASE Guidelines and Standards: Recommendations for Noninvasive Evaluation of Native Valvular Regurgitation—A Report from the American Society of Echocardiography Developed in Collaboration with the Society for Cardiovascular Magnetic Resonance, Journal of the American Society of Echocardiography, April 2017). After heparin reversal, no paravalvular leakage was detected by either echocardiography or angiography. Upon explant, the space between the outer skirt and the attached annuloplasty rings had become completely sealed by thrombus formation, and the head of the cable tie had become at least partially encapsulated by one or more thrombi.

For both the first and second prosthetic valves including fringed skirts, the immediate acute reduction in paravalvular leakage may be attributable to interaction between blood and the yarn filaments. The continued gradual reduction in paravalvular leakage observed for the second prosthetic valve post-heparin reversal may be attributable to a continued cellular-level biological response resulting in thrombus formation and sealing. For the first prosthetic valve with the yarn density of 300 yarns per inch, the sealing of the space between the frame and the annuloplasty rings occurred nearly immediately. For the second prosthetic valve with the yarn density of 150 yarns per inch, the time to full closure or sealing of the space between the frame and the annuloplasty rings (e.g., no detectable paravalvular leakage) was 5 to 30 minutes.

For the control prosthetic valve that had no outer skirt, paravalvular leakage having a grade of 2+ or greater was observed under heparinization. After heparin reversal, paravalvular leakage having an angiographic grade of 2+ to 3+ was observed. Upon explant, the space between the annuloplasty rings and the frame of the prosthetic valve was fully open or patent, and no appreciable biological sealing had occurred.

General Considerations

Any of the sealing element embodiments disclosed herein can be used in combination with any of the disclosed prosthetic heart valve and/or frame embodiments. A prosthetic heart valve can also include any of the sealing elements described herein, or portions thereof, in any combination.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, in certain configurations the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. An implantable prosthetic valve that is radially collapsible to a collapsed configuration and radially expandable to an expanded configuration, the prosthetic valve comprising:
    an annular frame having an inflow end, an outflow end, and a longitudinal axis;
    a leaflet structure positioned within the frame and secured thereto; and
    a sealing element secured to the frame, the sealing element comprising:
        a first woven portion extending circumferentially around the frame, the first woven portion comprising a plurality of interwoven filaments;
        a second woven portion extending circumferentially around the frame and spaced apart from the first woven portion in a downstream direction along the longitudinal axis of the frame;
        wherein at least a portion of the filaments exit a weave of the first woven portion and form loops extending radially outwardly from the frame, and extending in the downstream direction along the longitudinal axis of the frame to the second woven portion.

2. The prosthetic valve of claim 1, wherein:
    the sealing element comprises a first row of loops extending between the first woven portion and the second woven portion; and
    the sealing element comprises a second row of loops spaced apart from the first row of loops in the downstream.

3. The prosthetic valve of claim 2, wherein:
    the plurality of interwoven filaments of the first woven portion further comprises at least one first filament interwoven with a plurality of second filaments; and
    a portion of the at least one first filament forms the loops of the first woven portion.

4. The prosthetic valve of claim 3, wherein the second filaments are warp yarns and the at least one first filament is a weft yarn.

5. The prosthetic valve of claim 4, wherein at least one of the warp and weft yarns comprise textured yarns.

6. The prosthetic valve of claim 4, wherein the warp and weft yarns comprise fibers, the fibers having a diameter of from 1 μm to 20 μm to promote thrombus formation around the sealing element.

7. The prosthetic valve of claim 1, wherein the filaments that form the loops exit the weave of the first woven portion and are incorporated into a weave of the second woven portion such that the loops form a floating yarn portion between the first and second woven portions.

8. The prosthetic valve of claim 7, wherein the floating yarn portion comprises a first layer of loops and a second layer of loops radially outward of the first layer of loops.

9. The prosthetic valve of claim 8, wherein:
    the sealing element comprises a first fabric strip, a second fabric strip, and a third fabric strip;
    a plurality of the filaments that form the loops extend between the first fabric strip and the second fabric strip;
    a plurality of the filaments that form the loops extend between the second fabric strip and the third fabric strip; and
    the sealing element is folded about the second fabric strip such that the first fabric strip and the third fabric strip are adjacent each other to form the first woven portion, the filaments extending between the first fabric strip and the second fabric strip form the first layer of loops, and the filaments extending between the second fabric strip and the third fabric strip form the second layer of loops.

10. The prosthetic valve of claim 1, wherein the sealing element is secured to the frame such that the filaments that exit the weave of the first woven portion form the loops when the frame is in the expanded configuration, and are pulled straight when the frame is in the collapsed configuration.

11. A method, comprising:
    mounting the prosthetic valve of claim 1 to a distal end portion of a delivery apparatus;
    advancing the delivery apparatus through a patient's vasculature to the heart; and
    expanding the prosthetic valve in a native heart valve of the heart such that the prosthetic valve regulates blood flow through the native heart valve.

12. The prosthetic valve of claim 1, wherein the filaments forming the loops are oriented along the longitudinal axis of the frame.

13. The prosthetic valve of claim 1, wherein the loops form curves open toward the frame.

14. The prosthetic valve of claim 13, wherein a curvature of the loops is defined at least in part by a distance between the first woven portion and the second woven portion along the longitudinal axis of the frame.

15. The prosthetic valve of claim 1, wherein the loops form a non-woven portion of the sealing element located between the first woven portion and the second woven portion.

16. The prosthetic valve claim 7, wherein the floating yarn portion is configured to provide compressible volume when the frame is in the expanded configuration.

17. The prosthetic valve claim 16, wherein a thickness of the floating yarn portion is configured to decrease as the frame moves between the expanded configuration and the collapsed configuration.

18. The prosthetic valve of claim 7, wherein the floating yarn portion is one of a plurality of discrete floating yarn portions spaced apart from each other along the longitudinal axis of the frame.

19. The prosthetic valve of claim 1, wherein at least one of the first woven portion and the second woven portion comprises a leno weave pattern.

20. The prosthetic valve of claim 1, wherein the sealing element further comprises a third woven portion comprising a leno weave pattern and a plain weave pattern.

* * * * *